United States Patent
Himmelsbach et al.

(10) Patent No.: US 7,456,189 B2
(45) Date of Patent: *Nov. 25, 2008

(54) BICYCLIC HETEROCYCLES, MEDICAMENTS CONTAINING THESE COMPOUNDS, THEIR USE AND PROCESSES FOR THEIR PREPARATION

(75) Inventors: Frank Himmelsbach, Mittelbiberach (DE); Birgit Jung, Laupheim (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 484 days.

This patent is subject to a terminal disclaimer.

(21) Appl. No.: 10/947,854

(22) Filed: Sep. 23, 2004

(65) Prior Publication Data

US 2005/0070560 A1    Mar. 31, 2005

Related U.S. Application Data

(60) Provisional application No. 60/514,799, filed on Oct. 27, 2003.

(30) Foreign Application Priority Data

Sep. 30, 2003   (DE) ................ 103 45 875

(51) Int. Cl.
A61K 31/517 (2006.01)
C07D 239/72 (2006.01)
C07D 239/94 (2006.01)

(52) U.S. Cl. ............ 514/266.4; 514/266.2; 514/266.22; 514/266.24; 544/283; 544/293

(58) Field of Classification Search ............ 514/266.22, 514/266.24, 266.2, 266.4; 544/283, 293
See application file for complete search history.

(56) References Cited

U.S. PATENT DOCUMENTS

| | | | |
|---|---|---|---|
| 5,747,498 A | 5/1998 | Schnur et al. | |
| 5,770,599 A | 6/1998 | Gibson | |
| 5,866,572 A | 2/1999 | Barker et al. | |
| 6,362,336 B1 | 3/2002 | Lohmann et al. | |
| 6,399,602 B1 | 6/2002 | Barker et al. | |
| 6,414,148 B1 | 7/2002 | Thomas et al. | |
| 6,617,329 B2 | 9/2003 | Himmelsbach et al. | |
| 6,627,634 B2 | 9/2003 | Himmelsbach et al. | |
| 6,645,969 B1* | 11/2003 | Myers et al. ............. | 514/230.5 |
| 6,656,946 B2 | 12/2003 | Himmelsbach et al. | |
| 6,924,285 B2 | 8/2005 | Himmelsbach et al. | |
| 7,196,091 B2 | 3/2007 | Himmelsbach et al. | |
| 2002/0049197 A1 | 4/2002 | Himmelsbach et al. | 514/217.06 |
| 2002/0082271 A1 | 6/2002 | Himmelsbach et al. | 514/266.24 |
| 2002/0177601 A1 | 11/2002 | Himmelsbach et al. .. | 514/266.2 |
| 2003/0149062 A1 | 8/2003 | Jung et al. | |
| 2004/0048880 A1 | 3/2004 | Himmelsbach et al. .. | 514/266.2 |
| 2005/0070560 A1 | 3/2005 | Himmelsbach et al. | |
| 2005/0159436 A1 | 7/2005 | Himmelsbach et al. | |
| 2005/0182043 A1* | 8/2005 | Himmelsbach et al. | 514/211.15 |
| 2006/0264450 A1* | 11/2006 | Himmelsbach et al. .. | 514/266.2 |
| 2006/0270672 A1* | 11/2006 | Himmelsbach et al. .. | 514/234.2 |

FOREIGN PATENT DOCUMENTS

| | | |
|---|---|---|
| EP | 0566226 A1 | 10/1993 |
| EP | 0787722 A1 | 8/1997 |
| WO | 9633980 A1 | 10/1996 |
| WO | 9722596 A1 | 6/1997 |
| WO | 9730035 A1 | 8/1997 |
| WO | 9732856 A1 | 9/1997 |
| WO | 9738983 A1 | 10/1997 |
| WO | 9813354 A1 | 4/1998 |
| WO | 9843960 A1 | 10/1998 |
| WO | 9901467 A2 | 1/1999 |
| WO | 9906396 A1 | 2/1999 |
| WO | 9909016 A1 | 2/1999 |
| WO | 0018740 A1 | 4/2000 |
| WO | 0051991 A1 | 9/2000 |
| WO | WO 00/55141 | 9/2000 |
| WO | 0078735 A1 | 12/2000 |
| WO | 0177085 A1 | 10/2001 |
| WO | 0177104 A1 | 10/2001 |
| WO | WO 02/18351 A1 | 3/2002 |
| WO | WO 02/18372 A1 | 3/2002 |
| WO | 0250043 A1 | 6/2002 |
| WO | WO 03/082290 | 10/2003 |

OTHER PUBLICATIONS

Goldkorn, T. et al. "EGF-Receptor Phosphorylation . . . " Am. J. Respri. Cell. Mol. Biol., 1998, vol. 19, pp. 786-798.*
Tang, P.A. et. al. "A review of erlotinib and its clinical use" Expert Opinion Pharmacotherapy, 2006, vol. 7, No. 2, pp. 177-193.*
International Search Report Reference #PCT/EP2004/010723.

* cited by examiner

*Primary Examiner*—James O. Wilson
*Assistant Examiner*—Tamthom N Truong
(74) *Attorney, Agent, or Firm*—Michael P. Morris; Mary-Ellen M. Devlin; Alan R. Stempel

(57) ABSTRACT

Compounds of the formula

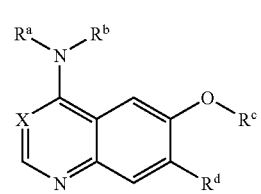

(I)

having an inhibitory action on the signal transduction mediated by tyrosine kinases, and being useful for the treatment of oncoses and of benign prostate hyperplasia (BPH), of diseases of the lung and of the airways. Exemplary compounds are:
(R)-4-(1-Phenylethylamino)-6-[1-(tert-butyloxycarbonyl)piperidin-4-yloxy]-7-methoxy-quinazoline and
(R)-4-(1-Phenylethylamino)-6-(piperidin-4-yloxy)-7-methoxyquinazoline dihydrochloride.

8 Claims, No Drawings

BICYCLIC HETEROCYCLES, MEDICAMENTS CONTAINING THESE COMPOUNDS, THEIR USE AND PROCESSES FOR THEIR PREPARATION

RELATED APPLICATIONS

This application claims benefit of U.S. Ser. No. 60/514,799, filed Oct. 27, 2003.

FIELD OF THE INVENTION

The present invention relates to bicyclic heterocycles of the general formula

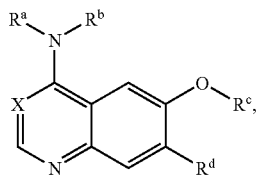

(I)

their tautomers, their stereoisomers, their mixtures and their salts, in particular their physiologically tolerable salts with inorganic or organic acids, which have valuable pharmacological properties, in particular an inhibitory action on the signal transduction mediated by tyrosine kinases, their use for the treatment of illnesses, in particular of oncoses and of benign prostate hyperplasia (BPH), of diseases of the lung and of the airways, and their preparation.

In the above general formula I $R^a$ is a hydrogen atom or a $C_{1-4}$-alkyl group, $R^b$ is a 1-phenylethyl group, in which the phenyl nucleus is in each case substituted by the groups $R^1$ to $R^3$, where $R^1$ and $R^2$, which can be identical or different, are in each case a hydrogen, fluorine, chlorine, bromine or iodine atom, a $C_{1-4}$-alkyl, hydroxyl, $C_{1-4}$-alkoxy, $C_{2-3}$-alkenyl or $C_{2-3}$-alkynyl group, an aryl, aryloxy, arylmethyl or arylmethoxy group, a heteroaryl, heteroaryloxy, heteroarylmethyl or heteroarylmethoxy group, a methyl or methoxy group substituted by 1 to 3 fluorine atoms or a cyano, nitro or amino group, and $R^3$ is a hydrogen, fluorine, chlorine or bromine atom or a methyl or trifluoromethyl group, $R^c$ is a cyclobutyl, cyclopentyl or cyclohexyl group, which is in each case substituted by a group $R^4$—N—$R^5$, where $R^4$ is a hydrogen atom or a $C_{1-3}$-alkyl group and $R^5$ is a hydrogen atom or a $C_{1-3}$-alkyl group, an aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, pyrrolidin-1-ylcarbonyl-$C_{1-3}$-alkyl, piperidin-1-ylcarbonyl-$C_{1-3}$-alkyl, homopiperidin-1-ylcarbonyl-$C_{1-3}$-alkyl, morpholin-4-ylcarbonyl-$C_{1-3}$-alkyl, homomorpholin-4-ylcarbonyl-$C_{1-3}$-alkyl, piperazin-1-ylcarbonyl-$C_{1-3}$-alkyl, 4-$C_{1-3}$-alkylpiperazin-1-ylcarbonyl-$C_{1-3}$-alkyl, homopiperazin-1-ylcarbonyl-$C_{1-3}$-alkyl or a 4-$C_{1-3}$-alkylhomopiperazin-1-ylcarbonyl-$C_{1-3}$-alkyl group, a hydroxy-$C_{2-4}$-alkyl, $C_{1-3}$-alkyloxy-$C_{2-4}$-alkyl, $C_{1-4}$-alkyloxycarbonylamino-$C_{2-4}$-alkyl, amino-$C_{2-4}$-alkyl, $C_{1-3}$-alkylamino-$C_{2-4}$-alkyl, di-($C_{1-3}$-alkyl)amino-$C_{2-4}$-alkyl, $C_{1-3}$-alkylcarbonylamino-$C_{2-4}$-alkyl, aminocarbonylamino-$C_{2-4}$-alkyl, $C_{1-3}$-alkyl-aminocarbonylamino-$C_{2-4}$-alkyl, di-($C_{1-3}$-alkyl)aminocarbonylamino-$C_{2-4}$-alkyl, pyrrolidin-1-ylcarbonylamino-$C_{2-4}$-alkyl, piperidin-1-ylcarbonylamino-$C_{2-4}$-alkyl, morpholin-4-ylcarbonylamino-$C_{2-4}$-alkyl, $C_{1-3}$-alkylsulphonyl-$C_{2-4}$-alkyl or a $C_{1-3}$-alkylsulphonylamino-$C_{2-4}$-alkyl group, a (2-oxopyrrolidin-1-yl)-$C_{2-4}$-alkyl, (2-oxopiperidin-1-yl)-$C_{2-4}$-alkyl, (3-oxo-morpholin-4-yl)-$C_{2-4}$-alkyl, (2-oxoimidazolidin-1-yl)-$C_{2-4}$-alkyl, (2-oxo-3-$C_{1-3}$-alkyl-imidazolidin-1-yl)-$C_{2-4}$-alkyl, (2-oxohexahydropyrimidin-1-yl)-$C_{2-4}$-alkyl or a (2-oxo-3-$C_{1-3}$-alkylhexahydropyrimidin-1-yl)-$C_{2-4}$-alkyl group, a $C_{1-4}$-alkylsulphonyl, chloro-$C_{1-4}$-alkylsulphonyl, bromo-$C_{1-4}$-alkylsulphonyl, amino-$C_{1-4}$-alkylsulphonyl, $C_{1-3}$-alkylamino-$C_{1-4}$-alkylsulphonyl, di-($C_{1-3}$-alkyl)-amino-$C_{1-4}$-alkylsulphonyl, (pyrrolidin-1-yl)-$C_{1-4}$-alkylsulphonyl, (piperidin-1-yl)-$C_{1-4}$-alkylsulphonyl, (homopiperidin-1-yl)-$C_{1-4}$-alkylsulphonyl, (morpholin-4-yl)-$C_{1-4}$-alkylsulphonyl, (homomorpholin-4-yl)-$C_{1-4}$-alkylsulphonyl, (piperazin-1-yl)-$C_{1-4}$-alkylsulphonyl, (4-$C_{1-3}$-alkylpiperazin-1-yl)-$C_{1-4}$-alkylsulphonyl, (homo-piperazin-1-yl)-$C_{1-4}$-alkylsulphonyl or a (4-$C_{1-3}$-alkylhomopiperazin-1-yl)-$C_{1-4}$-alkylsulphonyl group, a $C_{1-4}$-alkyloxycarbonyl group, a formyl, $C_{1-4}$-alkylcarbonyl, $C_{1-3}$-alkyloxy-$C_{1-4}$-alkylcarbonyl, tetrahydrofuranyl-carbonyl, tetrahydropyranylcarbonyl, amino-$C_{1-4}$-alkylcarbonyl, $C_{1-3}$-alkylamino-$C_{1-4}$-alkylcarbonyl, di-($C_{1-3}$-alkyl)amino-$C_{1-4}$-alkylcarbonyl, pyrrolidin-1-yl-$C_{1-4}$-alkylcarbonyl, piperidin-1-yl-$C_{1-4}$-alkylcarbonyl, (homopiperidin-1-yl)-$C_{1-4}$-alkylcarbonyl, morpholin-4-yl-$C_{1-4}$-alkylcarbonyl, (homomorpholin-4-yl)-$C_{1-4}$-alkylcarbonyl, (piperazin-1-yl)-$C_{1-4}$-alkylcarbonyl, (4-$C_{1-3}$-alkylpiperazin-1-yl)-$C_{1-4}$-alkylcarbonyl, (homopiperazin-1-yl)-$C_{1-4}$-alkylcarbonyl, (4-$C_{1-3}$-alkyl-homopiperazin-1-yl)-$C_{1-4}$-alkylcarbonyl or a $C_{1-3}$-alkylsulphonyl-$C_{1-4}$-alkylcarbonyl group, a cyano, aminocarbonyl, $C_{1-3}$-alkylaminocarbonyl, di-($C_{1-3}$-alkyl)aminocarbonyl, ($C_{1-3}$-alkyloxy-$C_{2-4}$-alkyl)aminocarbonyl, N—($C_{1-3}$-alkyl)-N—($C_{1-3}$-alkyloxy-$C_{2-4}$-alkyl)-aminocarbonyl, arylaminocarbonyl, pyrrolidin-1-ylcarbonyl, piperidin-1-ylcarbonyl, homopiperidin-1-ylcarbonyl, morpholin-4-ylcarbonyl, homomorpholin-4-yl-carbonyl, 2-oxa-5-azabicyclo[2.2.1]hept-5-ylcarbonyl, 3-oxa-8-azabicyclo[3.2.1]oct-8-ylcarbonyl, 8-oxa-3-azabicyclo[3.2.1]oct-3-ylcarbonyl, piperazin-1-yl-carbonyl, 4-$C_{1-3}$-alkylpiperazin-1-ylcarbonyl, homopiperazin-1-ylcarbonyl, 4-$C_{1-3}$-alkylhomopiperazin-1-ylcarbonyl, aminosulphonyl, $C_{1-3}$-alkyl-aminosulphonyl, di-($C_{1-3}$-alkyl)aminosulphonyl, pyrrolidin-1-yl-sulphonyl, piperidin-1-ylsulphonyl, homopiperidin-1-ylsulphonyl, morpholin-4-ylsulphonyl, homomorpholin-4-yl-sulphonyl, piperazin-1-ylsulphonyl, 4-$C_{1-3}$-alkylpiperazin-1-ylsulphonyl, homo-piperazin-1-ylsulphonyl or a 4-$C_{1-3}$-alkylhomopiperazin-1-ylsulphonyl group, a cyclobutyl, cyclopentyl or cyclohexyl group, which is in each case substituted by a group $R^6$, where $R^6$ is a 2-oxopyrrolidin-1-yl, 2-oxopiperidin-1-yl, 3-oxomorpholin-4-yl, 2-oxo-imidazolidin-1-yl, 2-oxo-3-$C_{1-3}$-alkylimidazolidin-1-yl, 2-oxohexahydropyrimidin-1-yl or a 2-oxo-3-$C_{1-3}$-alkylhexahydropyrimidin-1-yl group, an azetidin-3-yl group, which is substituted in the 1-position by the group $R^5$, where $R^5$ is defined as mentioned above, a pyrrolidin-3-yl group, which is substituted in the 1-position by the group $R^5$, where $R^5$ is defined as mentioned above, a piperidin-3-yl group, which is substituted in the 1-position by the group $R^5$, where $R^5$ is defined as mentioned above, a piperidin-4-yl group, which is substituted in the 1-position by the group $R^5$, where $R^5$ is defined as mentioned above, or a tetrahydrofuran-3-yl, tetrahydropyran-3-yl or tetrahydropyran-4-yl group, $R^d$ is a hydrogen atom or a fluorine, chlorine or bromine atom, a hydroxyl group, a $C_{1-4}$-alkyloxy group, a methoxy group substituted by 1 to 3 fluorine atoms, an ethyloxy group substituted by 1 to 5 fluorine atoms, a $C_{2-4}$-alkyloxy group, which is substituted by the group $R^6$ or $R^7$, where $R^6$ is defined as mentioned above and $R^7$ is a hydroxyl, $C_{1-3}$-alkyloxy, $C_{3-6}$-cycloalkyloxy, amino, $C_{1-3}$-alkylamino, di-($C_{1-3}$-alkyl)amino, bis(2-methoxyethyl)amino, pyrrolidin-1-yl, piperidin-1-yl, homopiperidin-1-yl, morpholin-4-yl, homomorpholin-4-yl, 2-oxa-5-azabicyclo-[2.2.1]hept-5-yl, 3-oxa-8-azabicyclo[3.2.1]oct-8-yl, 8-oxa-3-azabicyclo[3.2.1]oct-3-yl, piperazin-1-yl, 4-$C_{1-3}$-alkylpiperazin-1-yl, homopiperazin-1-yl or $C_{1-3}$-alkyl-homopiperazin-1-yl group, or a formylamino, $C_{1-4}$-alkylcarbonylamino, $C_{1-3}$-alkyloxy-$C_{1-3}$-alkylcarbonylamino, $C_{1-4}$-alkyloxycarbonylamino, aminocarbonylamino, $C_{1-3}$-alkylaminocarbonylamino, di-($C_{1-3}$-alkyl)aminocarbonylamino, pyrrolidin-1-ylcarbonylamino, piperidin-1-yl-carbonylamino, piperazin-1-ylcarbonylamino, 4-$C_{1-3}$-alkylpiperazin-1-ylcarbonyl-amino, morpholin-4-ylcarbonylamino or a $C_{1-4}$-alkylsulphonylamino group, a $C_{3-7}$-cycloalkyloxy or $C_{3-7}$-cycloalkyl-$C_{1-4}$-alkyloxy group, a tetrahydrofuran-3-yloxy, tetrahydropyran-3-yloxy or tetrahydropyran-4-yloxy group, a tetrahydrofuranyl-$C_{1-4}$-alkyloxy or tetrahydropyranyl-$C_{1-4}$-alkyloxy group, a $C_{1-4}$-alkoxy group, which is substituted by a pyrrolidinyl, piperidinyl or homopiperidinyl group substituted in the 1-position by the group $R^8$, where $R^8$ is a hydrogen atom or a $C_{1-3}$-alkyl group, or a $C_{1-4}$-alkoxy group, which is substituted by a morpholinyl group substituted in the 4-position by the group $R^8$, where $R^8$ is defined as mentioned above, and X is a methine group substituted by a cyano group or is a nitrogen atom, and where the aryl groups mentioned in the definition of the abovementioned groupgroups are in each case to be understood as meaning a phenyl group which is mono- or disubstituted by $R^9$, where the substituents can be identical or different and $R^9$ is a hydrogen atom, a fluorine, chlorine, bromine, or iodine atom or a $C_{1-3}$-alkyl, hydroxyl, $C_{1-3}$-alkyloxy, difluoromethyl, trifluoromethyl, difluoromethoxy, trifluoromethoxy or cyano group, the heteroaryl groups mentioned in the definition of the abovementioned groupgroups are to be understood as meaning a pyridyl, pyridazinyl, pyrimidinyl or pyrazinyl group, where the abovementioned heteroaryl groups are in each case mono- or disubstituted by the group $R^9$, where the substituents can be identical or different and $R^9$ is defined as mentioned above, and the abovementioned pyrrolidinyl, piperidinyl, piperazinyl and morpholinyl groups can in each case be substituted by one or two $C_{1-3}$-alkyl groups, and if not mentioned otherwise, the abovementioned alkyl groups can be straight-chain or branched.

Preferred compounds of the above general formula I are those in which $R^a$ is a hydrogen atom, $R^b$ is a 1-phenylethyl group, $R^c$ is a cyclopentyl group, which is substituted in the 3-position by a group $R^4$—N—$R^5$, where $R^4$ is a hydrogen atom or a $C_{1-3}$-alkyl group and $R^5$ is a hydrogen atom or a $C_{1-3}$-alkyl group, an aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, pyrrolidin-1-ylcarbonyl-$C_{1-3}$-alkyl, piperidin-1-ylcarbonyl-$C_{1-3}$-alkyl, piperazin-1-ylcarbonyl-$C_{1-3}$-alkyl, 4-$C_{1-3}$-alkylpiperazin-1-ylcarbonyl-$C_{1-3}$-alkyl or morpholin-4-ylcarbonyl-$C_{1-3}$-alkyl group, a hydroxy-$C_{2-4}$-alkyl, $C_{1-3}$-alkyloxy-$C_{2-4}$-alkyl, $C_{1-4}$-alkyloxycarbonylamino-$C_{2-4}$-alkyl, amino-$C_{2-4}$-alkyl, $C_{1-3}$-alkylamino-$C_{2-4}$-alkyl, di-($C_{1-3}$-alkyl)amino-$C_{2-4}$-alkyl, $C_{1-3}$-alkylcarbonylamino-$C_{2-4}$-alkyl, aminocarbonylamino-$C_{2-4}$-alkyl, $C_{1-3}$-alkyl-aminocarbonylamino-$C_{2-4}$-alkyl, di-($C_{1-3}$-alkyl)aminocarbonylamino-$C_{2-4}$-alkyl, morpholin-4-ylcarbonylamino-$C_{2-4}$-alkyl, $C_{1-3}$-alkylsulphonyl-$C_{2-4}$-alkyl or $C_{1-3}$-alkylsulphonylamino-$C_{2-4}$-alkyl group, a (2-oxopyrrolidin-1-yl)-$C_{2-4}$-alkyl, (2-oxopiperidin-1-yl)-$C_{2-4}$-alkyl, (3-oxo-morpholin-4-yl)-$C_{2-4}$-alkyl, (2-oxoimidazolidin-1-yl)-$C_{2-4}$-alkyl, (2-oxo-3-methylimidazolidin-1-yl)-$C_{2-4}$-alkyl, (2-oxohexahydropyrimidin-1-yl)-$C_{2-4}$-alkyl or (2-oxo-3-methylhexahydropyrimidin-1-yl)-$C_{2-4}$-alkyl group, a $C_{1-3}$-alkylsulphonyl, chloro-$C_{2-4}$-alkylsulphonyl, bromo-$C_{2-4}$-alkylsulphonyl, amino-$C_{2-4}$-alkylsulphonyl, $C_{1-3}$-alkylamino-$C_{2-4}$-alkylsulphonyl, di-($C_{1-3}$-alkyl)-amino-$C_{2-4}$-alkylsulphonyl, (pyrrolidin-1-yl)-$C_{2-4}$-alkylsulphonyl, (piperidin-1-yl)-$C_{2-4}$-alkylsulphonyl or (morpholin-4-yl)-$C_{2-4}$-alkylsulphonyl group, a $C_{1-4}$-alkyloxycarbonyl group, a formyl, $C_{1-3}$-alkylcarbonyl, $C_{1-3}$-alkyloxy-$C_{1-3}$-alkylcarbonyl, tetrahydrofuranyl-carbonyl, tetrahydropyranylcarbonyl, amino-$C_{1-3}$-alkylcarbonyl, $C_{1-3}$-alkylamino-$C_{1-3}$-alkylcarbonyl, di-($C_{1-3}$-alkyl)amino-$C_{1-3}$-alkylcarbonyl, pyrrolidin-1-yl-$C_{1-3}$-alkylcarbonyl, piperidin-1-yl-$C_{1-3}$-alkylcarbonyl, piperazin-1-yl-$C_{1-3}$-alkyl-carbonyl, 4-$C_{1-3}$-alkylpiperazin-1-yl-$C_{1-3}$-alkylcarbonyl, morpholin-4-yl-$C_{1-3}$-alkyl-carbonyl or a $C_{1-3}$-alkylsulphonyl-$C_{1-3}$-alkylcarbonyl group, a cyano, aminocarbonyl, $C_{1-3}$-alkylaminocarbonyl, di-($C_{1-3}$-alkyl)aminocarbonyl, ($C_{1-3}$-alkyloxy-$C_{2-4}$-alkyl) aminocarbonyl, N—($C_{1-3}$-alkyl)-N—($C_{1-3}$-alkyloxy-$C_{2-4}$-alkyl)-aminocarbonyl, phenylaminocarbonyl, pyrrolidin-1-ylcarbonyl, piperidin-1-yl-carbonyl, morpholin-4-ylcarbonyl, $C_{1-3}$-alkylmorpholin-4-ylcarbonyl, di-($C_{1-3}$-alkyl)morpholin-4-ylcarbonyl, homomorpholin-4-ylcarbonyl, 2-oxa-5-azabicyclo-[2.2.1]hept-5-ylcarbonyl, 3-oxa-8-azabicyclo[3.2.1]oct-8-ylcarbonyl, 8-oxa-3-aza-bicyclo[3.2.1]oct-3-ylcarbonyl, piperazin-1-ylcarbonyl, 4-($C_{1-3}$-alkyl)-piperazin-1-ylcarbonyl, aminosulphonyl, $C_{1-3}$-alkylaminosulphonyl, di-($C_{1-3}$-alkyl)amino-sulphonyl, pyrrolidin-1-yl-sulphonyl, piperidin-1-ylsulphonyl or a morpholin-4-ylsulphonyl group, or a cyclopentyl group, which is substituted in the 3-position by a group $R^6$, where
  $R^6$ is a 2-oxopyrrolidin-1-yl, 2-oxopiperidin-1-yl, 3-oxo-morpholin-4-yl, 2-oxo-imidazolidin-1-yl, 2-oxo-3-methylimidazolidin-1-yl, 2-oxohexahydropyrimidin-1-yl or a 2-oxo-3-methylhexahydropyrimidin-1-yl group,
a cyclohexyl group, which is substituted in the 3-position or in the 4-position by a group $R^4$—N—$R^5$, where $R^4$ and $R^5$ are defined as mentioned above,
a cyclohexyl group, which is substituted in the 3-position or in the 4-position by a group $R^6$, where $R^6$ is defined as mentioned above,
a pyrrolidin-3-yl group, which is substituted in the 1-position by the group $R^5$, where $R^5$ is defined as mentioned above,
a piperidin-3-yl group, which is substituted in the 1-position by the group $R^5$, where $R^5$ is defined as mentioned above,
a piperidin-4-yl group, which is substituted in the 1-position by the group $R^5$, where $R^5$ is defined as mentioned above, or
a tetrahydrofuran-3-yl, tetrahydropyran-3-yl or tetrahydropyran-4-yl group,
$R^d$ is a hydrogen atom,
a $C_{1-3}$-alkyloxy group,
a methoxy group, which is substituted by one to three fluorine atoms,
an ethyloxy group, which is substituted in the 2-position by a group $R^6$ or $R^7$, where $R^6$ is defined as mentioned above and
  $R^7$ is a hydroxyl, $C_{1-3}$-alkyloxy, amino, $C_{1-3}$-alkylamino, di-($C_{1-3}$-alkyl)amino, bis(2-methoxyethyl)amino, pyrrolidin-1-yl, piperidin-1-yl, morpholin-4-yl, homomorpholin-4-yl, 2-oxa-5-azabicyclo[2.2.1]hept-5-yl, 3-oxa-8-azabicyclo[3.2.1]oct-8-yl, 8-oxa-3-azabicyclo[3.2.1]oct-3-yl, piperazin-1-yl or a 4-$C_{1-3}$-alkylpiperazin-1-yl group, or
  a formylamino, $C_{1-4}$-alkylcarbonylamino, $C_{1-3}$-alkyloxy-$C_{1-3}$-alkylcarbonylamino, $C_{1-4}$-alkyloxycarbonylamino, aminocarbonylamino, $C_{1-3}$-alkylaminocarbonylamino, di-($C_{1-3}$-alkyl)aminocarbonylamino, pyrrolidin-1-ylcarbonylamino, piperidin-1-ylcarbonylamino, piperazin-1-ylcarbonylamino, 4-$C_{1-3}$-alkylpiperazin-1-yl-carbonylamino, morpholin-4-ylcarbonylamino or a $C_{1-4}$-alkylsulphonylamino group,
a propyloxy group, which is substituted in the 3-position by a group $R^6$ or $R^7$, where $R^6$ and $R^7$ are defined as mentioned above, or
a butyloxy group, which is substituted in the 4-position by a group $R^6$ or $R^7$, where $R^6$ and $R^7$ are defined as mentioned above, and
X is a nitrogen atom,
where, if not mentioned otherwise, the abovementioned alkyl groups can be straight-chain or branched,
their tautomers, their stereoisomers, their mixtures and their salts.

Particularly preferred compounds of the above general formula I are those in which
$R^a$ is a hydrogen atom,
$R^b$ is a 1-phenylethyl group,
$R^c$ is a cyclohexyl group, which is substituted in the 3-position or in the 4-position by a group $R^4$—N—$R^5$, where
  $R^4$ is a hydrogen atom, a methyl or ethyl group and
  $R^5$ is a hydrogen atom, a methyl, aminocarbonylmethyl, methylamino-carbonylmethyl, dimethylaminocarbonylmethyl, pyrrolidin-1-ylcarbonylmethyl, piperidin-1-ylcarbonylmethyl, piperazin-1-ylcarbonylmethyl, 4-methylpiperazin-1-ylcarbonylmethyl, morpholin-4-ylcarbonylmethyl, 2-(morpholin-4-yl-carbonyl)ethyl or 3-(morpholin-4-yl-carbonyl)propyl group,
  an ethyl, propyl, 2-hydroxyethyl, 3-hydroxypropyl, 2-methoxyethyl, 3-methoxy-propyl, 2-(butyloxycarbonylamino)ethyl, 2-aminoethyl, 3-aminopropyl, 2-(acetyl-amino)ethyl, 3-(acetylamino)propyl, 2-(ethylcarbonylamino)ethyl, 3-(ethyl-carbonylamino)propyl, 2-(propylcarbonylamino)ethyl, 3-(propylcarbonylamino)-propyl, 2-(ethylaminocarbonylamino)ethyl, 3-(ethylaminocarbonylamino)propyl, 2-(dimethylaminocarbonylamino)ethyl, 3-(dimethylaminocarbonylamino)propyl, 2-(morpholin-4-ylcarbonylamino)ethyl, 3-(morpholin-4-ylcarbonylamino)propyl, 2-(methylsulphonyl)ethyl, 3-(methylsulphonyl)propyl, 2-(methylsulphonylamino)-ethyl or a 3-(methylsulphonylamino)propyl group,
  a 2-(2-oxopyrrolidin-1-yl)ethyl, 2-(2-oxopiperidin-1-yl)ethyl, 2-(3-oxomorpholin-4-yl)ethyl, 2-(2-oxoimidazolidin-1-yl)ethyl, 2-(2-oxo-3-methylimidazolidin-1-yl)ethyl, 2-(2-oxohexahydropyrimidin-1-yl)ethyl or a 2-(2-oxo-3-methylhexahydropyrimidin-1-yl)ethyl group,
  a 3-(2-oxopyrrolidin-1-yl)propyl, 3-(2-oxopiperidin-1-yl)propyl, 3-(3-oxomorpholin-4-yl)propyl, 3-(2-oxoimidazolidin-1-yl)propyl, 3-(2-oxo-3-methylimidazolidin-1-yl)propyl, 3-(2-oxohexahydropyrimidin-1-yl)propyl or a 3-(2-oxo-3-methyl-hexahydropyrimidin-1-yl)propyl group,
  a methylsulphonyl, ethylsulphonyl, 3-chloropropylsulphonyl, 2-(morpholin-4-yl)-ethylsulphonyl or a 3-(morpholin-4-yl)-propylsulphonyl group,
  a propyloxycarbonyl or butyloxycarbonyl group,
  a formyl, acetyl, ethylcarbonyl, propylcarbonyl, methoxyacetyl, (2-methoxy-ethyl)carbonyl, (3-methoxypropyl)carbonyl, tetrahydrofuran-2-ylcarbonyl, tetrahydropyran-4-ylcarbonyl, aminoacetyl, methylaminoacetyl, dimethylamino-acetyl, morpholin-4-ylacetyl, [2-(morpholin-4-yl)ethyl]carbonyl, [3-(morpholin-4-yl)propyl]carbonyl or a methylsulphonylacetyl group,
  a cyano, aminocarbonyl, methylaminocarbonyl, dimethylaminocarbonyl, ethyl-aminocarbonyl, diethylaminocarbonyl, propylaminocarbonyl, (2-methoxyethyl)-aminocarbonyl, N-methyl-N-(2-methoxyethyl)aminocarbonyl, (3-methoxypropyl)-aminocarbonyl, N-methyl-N-(3-methoxypropyl)aminocarbonyl, phenylamino-carbonyl, pyrrolidin-1-ylcarbonyl, piperidin-1-ylcarbonyl, morpholin-4-ylcarbonyl, 2-methylmorpholin-4-ylcarbonyl, 2,6-dimethylmorpholin-4-ylcarbonyl, homo-morpholin-4-ylcarbonyl, 2-oxa-5-azabicyclo[2.2.1]hept-5-ylcarbonyl, 3-oxa-8-azabicyclo[3.2.1]oct-8-ylcarbonyl, 8-oxa-3-azabicyclo[3.2.1]oct-3-ylcarbonyl, 4-methylpiperazin-1-ylcarbonyl, aminosulphonyl, methylaminosulphonyl, dimethylaminosulphonyl or a morpholin-4-ylsulphonyl group,
a cyclohexyl group, which is substituted in the 3-position or in the 4-position by a group $R^6$, where
  $R^6$ is a 2-oxopyrrolidin-1-yl, 2-oxopiperidin-1-yl, 3-oxo-morpholin-4-yl, 2-oxo-imidazolidin-1-yl, 2-oxo-3-methylimidazolidin-1-yl, 2-oxohexachydropyrimidin-1-yl or a 2-oxo-3-methylhexahydropyrimidin-1-yl group,
a pyrrolidin-3-yl group, which is substituted in the 1-position by the group $R^5$, where $R^5$ is defined as mentioned above,
a piperidin-3-yl group, which is substituted in the 1-position by the group $R^5$, where $R^5$ is defined as mentioned above,
a piperidin-4-yl group, which is substituted in the 1-position by the group $R^5$, where $R^5$ is defined as mentioned above, a tetrahydrofuran-3-yl, tetrahydropyran-3-yl or tetrahydropyran-4-yl group, $R^d$ is a hydrogen atom, a methoxy, difluoromethoxy or ethyloxy group, an ethyloxy group, which is substituted in the 2-position by a group $R^6$ or $R^7$, where $R^6$ is defined as mentioned above and $R^7$ is a hydroxyl, methoxy, ethoxy, amino, dimethylamino, diethylamino, bis(2-methoxyethyl)amino, pyrrolidin-1-yl, piperidin-1-yl, morpholin-4-yl, homomorpholin-4-yl, 2-oxa-5-azabicyclo[2.2.1]hept-5-yl, 3-oxa-8-azabicyclo[3.2.1]oct-8-yl, 8-oxa-3-azabicyclo[3.2.1]oct-3-yl, piperazin-1-yl, 4-methylpiperazin-1-yl or 4-ethylpiperazin-1-yl group, or an acetylamino, ethylcarbonylamino, propylcarbonylamino, butylcarbonylamino, methoxyacetylamino, butyloxycarbonylamino, ethylaminocarbonylamino, dimethylaminocarbonylamino, pyrrolidin-1-ylcarbonylamino, piperidin-1-yl-carbonylamino, morpholin-4-ylcarbonylamino, methylsulphonylamino, ethyl-sulphonylamino or butylsulphonylamino group, a propyloxy group, which is substituted in the 3-position by a group $R^6$ or $R^7$, where $R^6$ and $R^7$ are defined as mentioned above, or a butyloxy group, which is substituted in the 4-position by a group $R^6$ or $R^7$, where $R^6$ and $R^7$ are defined as mentioned above, and X is a nitrogen atom, where, if not mentioned otherwise, the abovementioned alkyl groups can be straight-chain or branched, their tautomers, their stereoisomers, their mixtures and their salts.

Very particularly preferred compounds of the general formula I are those in which $R^a$ is a hydrogen atom, $R^b$ is a 1-phenylethyl group, $R^c$ is a cyclohexyl group, which is substituted in the 4-position by an amino, methylamino, dimethylamino, acetylamino, N-(acetyl)methylamino, methoxy-acetylamino, N-(methoxyacetyl)methylamino, tetrahydropyran-4-ylcarbonylamino, N-(tetrahydropyran-4-ylcarbonyl)methylamino, tert-butyloxycarbonylamino, N-(tert-butyloxycarbonyl)methylamino, N-(ethylaminocarbonyl)methylamino, dimethylamino-carbonylamino, N-(dimethylaminocarbonyl)methylamino, N-(piperidin-1-ylcarbonyl)-methylamino, morpholin-4-ylcarbonylamino, N-(morpholin-4-ylcarbonyl)methylamino, N-(4-methylpiperazin-1-ylcarbonyl)methylamino, methylsulphonylamino, N-(methyl-sulphonyl)methylamino, ethylsulphonylamino, N-(ethylsulphonyl)methylamino, dimethyl-aminosulphonylamino, N-(dimethylaminosulphonyl)methylamino, morpholin-4-ylsulphonylamino or N-(morpholin-4-ylsulphonyl)methylamino group, a pyrrolidin-3-yl group, a pyrrolidin-3-yl group, which is substituted in the 1-position by a tert-butyloxycarbonyl or methylsulphonyl group, a piperidin-3-yl group, a piperidin-3-yl group, which is substituted in the 1-position by a tert-butyloxycarbonyl or methylsulphonyl group, a piperidin-4-yl group, a piperidin-4-yl group, which is substituted in the 1-position by a methyl, (aminocarbonyl)methyl, (dimethylaminocarbonyl)methyl, (morpholin-4-ylcarbonyl)-methyl, 2-(tert-butyloxycarbonylamino)ethyl, 2-aminoethyl, 2-(acetylamino)ethyl, 2-(methylsulphonylamino)ethyl, cyano, acetyl, methoxyacetyl, (dimethylamino)acetyl, (morpholin-4-yl)acetyl, tetrahydropyran-4-ylcarbonyl, ethylaminocarbonyl, isopropyl-aminocarbonyl, dimethylaminocarbonyl, diethylaminocarbonyl, pyrrolidin-1-ylcarbonyl, piperidin-1-ylcarbonyl, morpholin-4-ylcarbonyl, 2-methylmorpholin-4-ylcarbonyl, 2,6-di-methylmorpholin-4-ylcarbonyl, homomorpholin-4-ylcarbonyl, 4-methylpiperazin-1-yl-carbonyl, isopropyloxycarbonyl, tert-butyloxycarbonyl, methylsulphonyl, dimethylaminosulphonyl or morpholin-4-ylsulphonyl group, or a tetrahydrofuran-3-yl, tetrahydropyran-3-yl or tetrahydropyran-4-yl group, $R^d$ is a methoxy, ethyloxy or a 2-(methoxy)ethyloxy group, and X is a nitrogen atom, their tautomers, their stereoisomers, their mixtures and their salts.

Especially preferred compounds of the general formula I are those in which $R^a$ is a hydrogen atom, $R^b$ is a 1-phenylethyl group, $R^c$ is a piperidin-4-yl group, a piperidin-4-yl group, which is substituted in the 1-position by a methyl, cyano, acetyl, morpholin-4-ylcarbonyl, tert-butyloxycarbonyl or methylsulphonyl group, $R^d$ is a methoxy group and X is a nitrogen atom, their tautomers, their stereoisomers, their mixtures and their salts.

The compounds of the general formula I can be prepared, for example, by the following processes:

a) reaction of a compound of the general formula $$\underset{\text{(II)}}{\begin{array}{c}R^a \diagdown N \diagup R^b \\ \text{quinoline-O-H with } R^d\end{array}}$$

in which $R^a$, $R^b$, $R^d$ and X are defined as mentioned at the outset, with a compound of the general formula $$Z^1\text{-}R^c \qquad (III)$$

in which $R^c$ is defined as mentioned at the outset and $Z^1$ is a leaving group such as a halogen atom, e.g. a chlorine or bromine atom, a sulphonyloxy group such as a methanesulphonyloxy or p-toluenesulphonyloxy group or a hydroxyl group.

Using a compound of the general formula III in which $Z^1$ is a hydroxyl group, the reaction is carried out in the presence of a dehydrating agent, preferably in the presence of a phosphine and of an azodicarboxylic acid derivative such as, for example, triphenylphosphine/diethyl azodicarboxylate, expediently in a solvent such as methylene chloride, acetonitrile, tetrahydrofuran, dioxane, toluene or ethylene glycol diethyl ether at temperatures between −50 and 150° C., but preferably at temperatures between −20 and 80° C.

b) For the preparation of compounds of the general formula I, in which $R^d$ is one of the optionally substituted alkyloxy groups mentioned at the outset:

reaction of a compound of the general formula

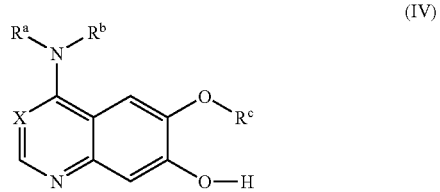

in which $R^a$, $R^b$, $R^c$ and X are defined as mentioned at the outset, with a compound of the general formula

in which $R^{d'}$ is a $C_{1-4}$-alkyl group, a methyl group substituted by 1 to 3 fluorine atoms, an ethyl group substituted by 1 to 5 fluorine atoms, a $C_{2-4}$-alkyl group substituted by a group $R^6$ or $R^7$, where $R^6$ and $R^7$ are defined as mentioned at the outset, a $C_{1-4}$-alkyl group, which is substituted by a pyrrolidinyl, piperidinyl or homopiperidinyl group substituted in the 1-position by the group $R^8$, or a $C_{1-4}$-alkyl group, which is substituted by a morpholinyl group substituted in the 4-position by the group $R^8$, where $R^8$ is in each case defined as mentioned at the outset, and $Z^2$ is a leaving group such as a halogen atom, an alkylsulphonyloxy, arylsulphonyloxy or a hydroxyl group.

If the leaving group is a halogen atom such as a chlorine, bromine or iodine atom or an alkylsulphonyloxy or arylsulphonyloxy group such as the methanesulphonyloxy or p-toluenesulphonyloxy group, the reaction is preferably carried out in the presence of an organic or inorganic base such as potassium carbonate, sodium hydride or N-ethyl-diisopropylamine. If the leaving group is a hydroxyl group, then the reaction is carried out in the presence of a dehydrating agent, preferably in the presence of a phosphine and of an azodicarboxylic acid derivative such as, for example, triphenyl-phosphine/diethyl azodicarboxylate.

c) For the preparation of compounds of the general formula I, in which $R^d$ is one of the alkyloxy groups mentioned at the outset, which is substituted by an optionally substituted amino, alkylamino or dialkylamino group or by an optionally substituted heterocyclic group bonded via an imino nitrogen atom:

reaction of a compound of the general formula

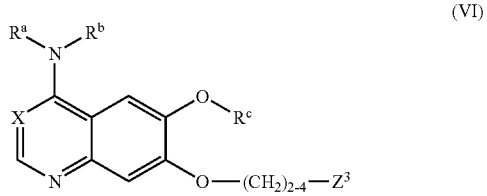

in which $R^a$, $R^b$, $R^c$ and X are defined as mentioned at the outset and $Z^3$ is a leaving group such as a halogen atom, e.g. a chlorine or bromine atom or a sulphonyloxy group such as a methanesulphonyloxy or p-toluenesulphonyloxy group, with ammonia, an appropriate, optionally substituted alkylamine, dialkylamine or an imino compound or their suitable salts or derivatives, such as, for example, morpholine.

d) For the preparation of compounds of the general formula I, in which $R^d$ is a hydroxyl group:

cleavage of a protective group from a compound of the general formula

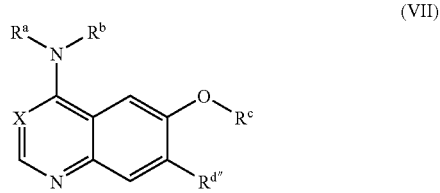

in which $R^a$, $R^b$, $R^c$ and X are defined as mentioned at the outset and $R^{d''}$ is a group which can be converted into a hydroxyl group, for example an optionally substituted benzyloxy group, a trimethylsilyloxy, acetyloxy, benzoyloxy, methoxy, ethoxy, tert-butoxy or trityloxy group.

The cleavage of the protective group is carried out, for example, hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali base such as sodium hydroxide or potassium hydroxide or aprotically, e.g. in the presence of iodotrimethylsilane, at temperatures between 0 and 120° C., preferably at temperatures between 10 and 100° C.

The cleavage of a benzyl or methoxybenzyl group is carried out, for example, hydrogenolytically, e.g. with hydrogen in the presence of a catalyst such as palladium/carbon in a suitable solvent such as methanol, ethanol, ethyl acetate or glacial acetic acid optionally with addition of an acid such as hydrochloric acid at temperatures between 0 and 100° C., but preferably at room temperatures between 20 and 60° C., and at a hydrogen pressure of 1 to 7 bar, but preferably of 3 to 5 bar. The cleavage of a 2,4-dimethoxybenzyl group, however, is preferably carried out in trifluoroacetic acid in the presence of anisole.

The cleavage of a tert-butyl or benzyl group is carried out, for example, by treatment with an acid such as trifluoroacetic acid, hydrochloric acid or hydrobromic acid or by treatment with iodotrimethylsilane optionally using a solvent such as methylene chloride, dioxane, methanol or diethyl ether.

e) For the preparation of compounds of the general formula I, in which $R^c$ contains an —NH group:

cleavage of a protective group from a compound of the general formula

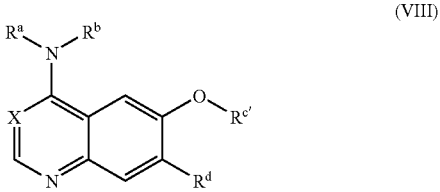

in which $R^a$, $R^b$, $R^d$ and X are defined as mentioned at the outset and $R^{c'}$ has the meanings mentioned at the outset for $R^c$ with the proviso that $R^c$ contains a protected nitrogen atom.

Customary protective groupgroups for an amino, alkylamino or imino group are, for example, the formyl, acetyl, trifluoroacetyl, ethoxycarbonyl, tert-butoxycarbonyl, benzyloxycarbonyl, benzyl, methoxybenzyl or 2,4-dimethoxybenzyl group, where the phthalyl group is additionally possible for the amino group.

The cleavage of the protective group is carried out, for example, hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali base such as sodium hydroxide or potassium hydroxide or aprotically, e.g. in the presence of iodotrimethylsilane, at temperatures between 0 and 120° C., preferably at temperatures between 10 and 100° C.

The cleavage of a benzyl, methoxybenzyl or benzyloxycarbonyl group, however, is carried out, for example, hydrogenolytically, e.g. with hydrogen in the presence of a catalyst such as palladium/carbon in a suitable solvent such as methanol, ethanol, ethyl acetate or glacial acetic acid optionally with addition of an acid such as hydrochloric acid at temperatures between 0 and 100° C., but preferably at room temperatures between 20 and 60° C., and at a hydrogen pressure of 1 to 7 bar, but preferably of 3 to 5 bar. The cleavage of a 2,4-dimethoxybenzyl group, however, is preferably carried out in trifluoroacetic acid in the presence of anisole.

The cleavage of a tert-butyl- or tert-butyloxycarbonyl group is preferably carried out by treatment with an acid such as a trifluoroacetic acid or hydrochloric acid or by treatment with iodotrimethylsilane optionally using a solvent such as methylene chloride, dioxane, methanol or diethyl ether.

The cleavage of a trifluoroacetyl group is preferably carried out by treatment with an acid such as hydrochloric acid optionally in the presence of a solvent such as acetic acid at temperatures between 50 and 120° C. or by treatment with sodium hydroxide solution optionally in the presence of a solvent such as tetrahydrofuran at temperatures between 0 and 50° C.

The cleavage of a phthalyl group is preferably carried out in the presence of hydrazine or of a primary amine such as methylamine, ethylamine or n-butylamine in a solvent such as methanol, ethanol, isopropanol, toluene/water or dioxane at temperatures between 20 and 50° C.

f) For the preparation of compounds of the general formula I, in which $R^c$ contains an alkyl group substituted by an optionally substituted amino, alkylamino or dialkylamino group or by an optionally substituted heterocyclic group bonded via a nitrogen atom:
reaction of a compound of the general formula

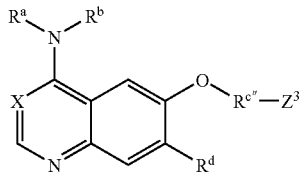

(IX)

in which $R^a$, $R^b$, $R^d$ and X are defined as mentioned at the outset, $Z^3$ is a leaving group, for example a halogen atom such as a chlorine or bromine atom, or a sulphonyloxy group such as a methanesulphonyloxy or p-toluenesulphonyloxy group, and $R^{''}c$ has the meanings mentioned at the outset for $R^c$, with the proviso that a hydrogen atom bonded to an aliphatic carbon atom is replaced by the group $Z^3$, with ammonia, an appropriate, optionally substituted alkylamine, dialkylamine or an imino compound or their suitable salts or derivatives, such as, for example, morpholine.

If, according to the invention, a compound of the general formula I is obtained which contains an amino, alkylamino or imino group, then this can be converted into a corresponding acyl, cyano or sulphonyl compound of the general formula I by means of acylation, cyanation or sulphonylation, where suitable acylating agents are, for example, isocyanates, carbamoyl chlorides, carboxylic acid halides, carboxylic acid anhydrides and carboxylic acids with activating agents such as N,N'-carbonyldiimidazole, N,N'-dicyclohexylcarbodiimide or O-(benzotriazol-1-yl)-N,N,N'N'-tetramethyluronium tetrafluoroborate, suitable sulphonylating agents are sulphonyl halides and suitable cyanating agents are cyanogen chloride or cyanogen bromide, and/or a compound of the general formula I, which contains an amino, alkylamino or imino group, then this can be converted into a corresponding alkyl compound of the general formula I by means of alkylation or reductive alkylation and/or a compound of the general formula I, which contains a chloro-$C_{1-4}$-alkylsulphonyl or bromo-$C_{1-4}$-alkylsulphonyl group, then this can be converted into a corresponding amino-$C_{1-4}$-alkylsulphonyl compound by reaction with an amine and/or a compound of the general formula I, which contains a tert-butyloxycarbonylamino, N-alkyl-N-(tert-butyloxycarbonyl)amino or a N-tert-butyloxycarbonylimino group, then this can be converted into a corresponding amino, alkylamino or imino compound of the general formula I by means of treatment with an acid such as hydrochloric acid or trifluoroacetic acid.

In the reaction as described above, reactive groups which may be present such as hydroxyl, amino, alkylamino or imino groups can be protected during the reaction by customary protective groups, which are cleaved again after the reaction.

For example, the trimethylsilyl, acetyl, trityl, benzyl or tetrahydropyranyl group is possible as a protective group for a hydroxyl group.

Possible protective groupgroups for an amino, alkylamino or imino group are, for example, the formyl, acetyl, trifluoroacetyl, ethoxycarbonyl, tert-butoxycarbonyl, benzyloxycarbonyl, benzyl, methoxybenzyl or 2,4-dimethoxybenzyl group.

The optionally subsequent cleavage of a used protective group is carried out, for example, hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali base such as sodium hydroxide or potassium hydroxide or aprotically, e.g. in the presence of iodotrimethylsilane, at temperatures between 0 and 120° C., preferably at temperatures between 10 and 100° C.

The cleavage of a benzyl, methoxybenzyl or benzyloxycarbonyl group, however, is carried out, for example, hydrogenolytically, e.g. with hydrogen in the presence of a catalyst such as palladium/carbon in a suitable solvent such as methanol, ethanol, ethyl acetate or glacial acetic acid optionally with addition of an acid such as hydrochloric acid at temperatures between 0 and 100° C., but preferably at room temperatures between 20 and 60° C., and at a hydrogen pressure of 1 to 7 bar, but preferably of 3 to 5 bar. The cleavage of a 2,4-dimethoxybenzyl group, however, is preferably carried out in trifluoroacetic acid in the presence of anisole.

The cleavage of a tert-butyl or tert-butyloxycarbonyl group is preferably carried out by treatment with an acid such as trifluoroacetic acid or hydrochloric acid or by treatment with iodotrimethylsilane optionally using a solvent such as methylene chloride, dioxane, methanol or diethyl ether.

The cleavage of a trifluoroacetyl group is preferably carried out by treatment with an acid such as hydrochloric acid optionally in the presence of a solvent such as acetic acid at temperatures between 50 and 120° C. or by treatment with sodium hydroxide solution optionally in the presence of a solvent such as tetrahydrofuran or methanol at temperatures between 0 and 50° C.

Further, the compounds of the general formula I obtained, such as have already been mentioned at the outset, can be separated into their enantiomers and/or diastereomers. Thus it is possible, for example, to separate cis/trans mixtures into their cis and trans isomers, and compounds having at least one optically active carbon atom into their enantiomers.

Thus, for example, the cis/trans mixtures obtained can be separated by chromatography into their cis and trans isomers, the compounds of the general formula I obtained, which occur in racemates, can be separated into their optical antipodes by methods known per se (see Allinger N. L. and Eliel E. L. in "Topics in Stereochemistry", Vol. 6, Wiley lnterscience, 1971)) and compounds of the general formula I having at least 2 asymmetric carbon atoms can be separated on the basis of their physicochemical differences by methods known per se, e.g. by chromatography and/or fractional crystallization, into their diastereomers, which, if they occur in racemic form, can subsequently be separated into the enantiomers as mentioned above.

The separation of enantiomers is preferably carried out by column separation on chiral phases or by recrystallizing from an optically active solvent or by reacting with an optically active substance forming salts or derivatives, such as, for example, esters or amides, with the racemic compound, in particular acids and their activated derivatives or alcohols, and separating the diastereomeric salt mixture or derivative obtained in this way, e.g. on the basis of different solubilities, where the free antipodes can be liberated from the pure diastereomeric salts or derivatives by the action of suitable agents. Particularly common, optically active acids are, for example, the D and L forms of tartaric acid or dibenzoyltartaric acid, di-O-p-tolyltartaric acid, malic acid, mandelic acid, camphorsulphonic acid, glutamic acid, aspartic acid or quinic acid. A possible optically active alcohol is, for example, (+)- or (−)-menthol and an optically active acyl group in amides is, for example, (+)- or (−)-menthyloxycarbonyl.

In addition, the compounds of the formula I obtained can be converted into their salts, in particular for pharmaceutical administration into their physiologically tolerable salts with inorganic or organic acids. Possible acids for this are, for example, hydrochloric acid, hydrobromic acid, sulphuric acid, methanesulphonic acid, phosphoric acid, fumaric acid, succinic acid, lactic acid, citric acid, tartaric acid or maleic acid.

The compounds of the general formulae II to IX used as starting substances are known from the literature or can be obtained by processes known per se from the literature or the processes described above, optionally with additional introduction of protective groupgroups (e.g. compounds of the formula IV or VII and VIII).

As already mentioned at the outset, the compounds of the general formula I according to the invention and their physiologically tolerable salts have valuable pharmacological properties, in particular an inhibitory action on the signal transduction mediated by the epidermal growth factor receptor (EGF-R), where this can be caused, for example, by an inhibition of ligand binding, receptor dimerization or tyrosine kinase itself. Moreover, it is possible that the signal transmission to components lying further downstream is blocked.

The biological properties of the novel compounds were tested as follows:

The inhibition of human EGF receptor kinase was determined with the aid of the cytoplasmatic tyrosine kinase domain (methionine 664 to alanine 1186 based on the sequence published in Nature 309 (1984), 418). For this, the protein was expressed in Sf9 insect cells as a GST fusion protein using the Baculovirus expression system.

The measurement of the enzyme activity was carried out in serial dilutions in the presence or absence of the test compounds. The polymer pEY (4:1) from SIGMA was used as a substrate. Biotinylated pEY (bio-pEY) was added as a tracer and substrate. Each 100 μl of reaction solution contained 10 μl of the inhibitor in 50% DMSO, 20 μl of the substrate solution (200 mM HEPES pH 7.4, 50 mM magnesium acetate, 2.5 mg/ml poly(EY), 5 μg/ml bio-pEY) and 20 μl of enzyme preparation. The enzyme reaction was started by addition of 50 μl of a 100 μM ATP solution in 10 mM magnesium chloride. The dilution of the enzyme preparation was adjusted such that the phosphate incorporation into the bio-pEY was linear with respect to time and amount of enzyme. The enzyme preparation was diluted in 20 mM HEPES pH 7.4, 1 mM EDTA, 130 mM sodium chloride, 0.05% Triton X-100, 1 mM DTT and 10% glycerol.

The enzyme assays were carried out at room temperature over a period of 30 minutes and ended by addition of 50 μl of a stop solution (250 mM EDTA in 20 mM HEPES pH 7.4). 100 μl were transferred to a streptavidin-coated microtitre plate and incubated at room temperature for 60 minutes. The plate was then washed with 200 μl of a wash solution (50 mM tris, 0.05% Tween 20). After addition of 100 μl of an HRPO-labelled anti-PY antibody (PY20H Anti-PTyr:HRP from Transduction Laboratories, 250 ng/ml) the mixture was incubated for 60 minutes. The microtitre plate was then washed three times with 200 μl each of wash solution. The samples were then treated with 100 μl of a TMB-peroxidase solution (A:B=1:1, Kirkegaard Perry Laboratories). The reaction was stopped after 10 minutes. The extinction was measured at $OD_{450\,nm}$ using an ELISA reader. All data points were determined as triplicates.

The data were fitted by means of an iterative calculation using an analysis program for sigmoidal curves (Graph Pad Prism Version 3.0). All analyses had a correlation coefficient of over 0.9. From the curves, the active compound concentration was derived which inhibits the activity of the EGF receptor kinase to 50% ($IC_{50}$).

The compounds of the general formula I according to the invention inhibit the signal transduction by tyrosine kinases, for example of the human EGF receptor, and are therefore useful for the treatment of pathophysiological processes which are caused by hyperfunction of tyrosine kinases. These are, for example, benign or malignant tumours, in particular tumours of epithelial and neuroepithelial origin, formation of metastases and the abnormal proliferation of vascular endothelial cells (neoangiogenesis).

The compounds according to the invention are also useful for the prevention and treatment of diseases of the airways and of the lung which are accompanied by increased or altered mucus production, which is caused by stimulation of tyrosine kinases, such as, for example, in inflammatory diseases of the airways such as acute bronchitis, chronic bronchitis, chronic obstructive bronchitis (COPD), coughing, pulmonary emphysema, allergic or non-allergic rhinitis or sinusitis, chronic sinusitis or rhinitis, asthma, allergic bronchitis, alveolitis, Farmer's disease, hyperreactive airways, bronchitis or pneumonitis caused by infections, such as, for example, bacteria or viruses, helminths, fungi or protozoa, paediatric asthma, bronchiectases, acute respiratory distress syndrome (ARDS), pulmonary oedema, bronchitis or pneumonitis or interstitial pneumonia or pulmonary fibrosis of various causes, such as, for example, as a result of aspiration, inhalation of toxic gases or vapours, as a result of heart failure, irradiation, chemotherapy, in lupus erythematosus, systemic scleroderma, asbestosis, silicosis, Besnier-Boeck disease or sarcoidosis, granulomatosis, idiopathic pulmonary fibrosis (IPF), cystic fibrosis or mucoviscidosis, or alpha1-antitrypsin deficiency or nasal polyps.

The compounds are also suitable for the treatment of diseases of the gastrointestinal tract and of the bile ducts and gall bladder, which are accompanied by a disturbed activity of the tyrosine kinases, such as are to be found, for example, in the case of chronic inflammatory changes, such as villous or adenomatous polyps of the gastrointestinal tract, polyps in familial polyposis coli, intestinal polyps in Gardner's syndrome, polyps in Peutz-Jeghers syndrome, inflammatory pseudopolyps, juvenile polyps, polyps in colitis cystica profunda and in pneumatosis cystoides intestinalis, acute or chronic cholecystitis, Crohn's disease, ulcerative colitis, ulcers or polyps of the gastrointestinal tract, diseases of the gastrointestinal tract which are accompanied by increased secretion, such as Ménétrier's disease, secretory adenoma or protein loss syndrome.

Moreover, the compounds of the general formula I and their physiologically tolerable salts can be used for the treatment of inflammatory diseases of the skin and of the joints which are caused by aberrant function of tyrosine kinases, such as, for example epidermal hyperproliferation (psoriasis) and arthritis, and for the treatment of benign prostate hyperplasia (BPH), diseases of the immune system and hyperproliferation in haematopoetic cells.

On account of their biological properties, the compounds according to the invention can be used alone or in combination with other pharmacologically active compounds, for example in tumour therapy in monotherapy or in combination with other antitumour therapeutics, for example in combination with topoisomerase inhibitors (e.g. etoposide), mitosis inhibitors (e.g. vinblastine), compounds interacting with nucleic acids (e.g. cis-platin, cyclophosphamide, adriamycin), hormone antagonists (e.g. tamoxifen), inhibitors of metabolic processes (e.g. 5-FU etc.), cytokines (e.g. interferons), antibodies etc. For the treatment of airway diseases, these compounds can be used alone or in combination with other airway therapeutics, such as, for example, compounds having secretolytic activity (e.g. ambroxole, N-acetylcysteine), broncholytic activity (e.g. tiotropium or ipratropium or fenoterol, salmeterol, salbutamol) and/or anti-inflammatory activity (e.g. theophylline or glucocorticoids). For the treatment of diseases in the region of the gastrointestinal tract, these compounds can likewise be given alone or in combination with motility- or secretion-influencing substances. These combinations can be administered either simultaneously or sequentially.

The administration of these compounds either alone or in combination with other active compounds can be carried out intravenously, subcutaneously, intramuscularly, intraperitoneally, intranasally, by inhalation or transdermally or orally, aerosol formulations being particularly suitable for inhalation.

In the case of pharmaceutical administration, the compounds according to the invention are as a rule used in warm-bloodied vertebrates, in particular in man, in doses of 0.01-100 mg/kg of body weight, preferably at 0.1-15 mg/kg. For administration, these are incorporated, e.g. with maize starch, lactose, sucrose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fat-containing substances such as hard fat or their suitable mixtures, into customary galenic preparations, such as tablets, coated tablets, capsules, powders, suspensions, solutions, sprays or suppositories.

The following examples are intended to illustrate the present invention in greater detail without restricting it:

Preparation of the Final Compounds:

EXAMPLE 1

(R)-4-(1-Phenylethylamino)-6-[1-(tert-butyloxycarbonyl)piperidin-4-yloxy]-7-methoxy-quinazoline

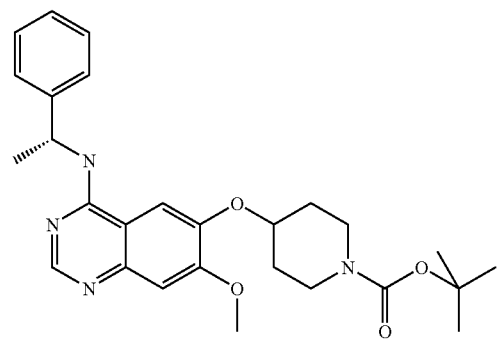

4.8 g of (R)-4-(1-phenylethylamino)-6-hydroxy-7-methoxyquinazoline (see WO 02/18351), 7.55 g of 1-(tert-butyloxycarbonyl)-4-(p-toluenesulphonyloxy)piperidine, 5.7 g of potassium carbonate and 50 ml dimethylformamide are stirred at 60° C. for 48 hours. The reaction mixture is diluted with 300 ml of ethyl acetate and extracted three times by shaking with water. The organic phase is washed with sodium chloride solution, dried and concentrated. The residue is purified by chromatography on a silica gel column using ethyl acetate/methanol/conc. aqueous ammonia.

Yield: 5.2 g (67% of theory)

$R_f$: 0.53 (silica gel, ethyl acetate/methanol/conc. aqueous ammonia=95:5:1)

Mass spectrum (ESI$^+$): m/z=479 [M+H]$^+$

EXAMPLE 2

(R)-4-(1-Phenylethylamino)-6-(piperidin-4-yloxy)-7-methoxyquinazoline dihydrochloride

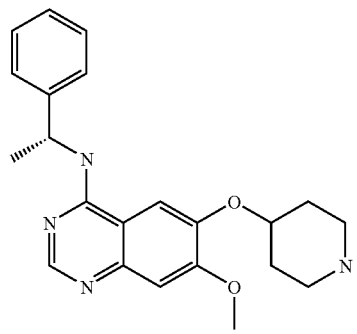

Prepared by treatment of (R)-4-(1-phenylethylamino)-6-[1-(tert-butyloxycarbonyl)-piperidin-4-yloxy]-7-methoxyquinazoline with 5M isopropanolic hydrochloric acid in methylene chloride at room temperature.

$R_f$: 0.52 (reversed phase silica gel RP8, acetonitrile/water/trifluoroacetic acid=50:50:1)

Mass spectrum (ESI$^+$): m/z=379 [M+H]$^+$

EXAMPLE 3

(R)-4-(1-Phenylethylamino)-6-(1-methylpiperidin-4-yloxy)-7-methoxyquinazoline

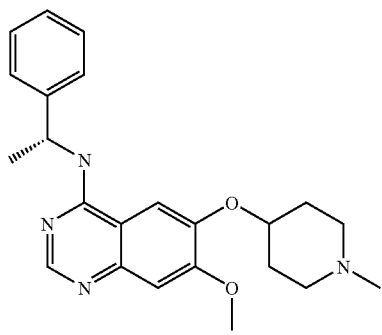

Prepared by treatment of (R)-4-(1-phenylethylamino)-6-(piperidin-4-yloxy)-7-methoxy-quinazoline dihydrochloride with formaldehyde, sodium triacetoxyborhydride and N-ethyldiisopropylamine in tetrahydrofuran.

$R_f$: 0.48 (reversed phase silica gel RP8, acetonitrile/water/trifluoroacetic acid=50:50:1)

Mass spectrum (ESI$^+$): m/z=393 [M+H]$^+$

EXAMPLE 4

(R)-4-(1-Phenylethylamino)-6-(1-acetylpiperidin-4-yloxy)-7-methoxyquinazoline

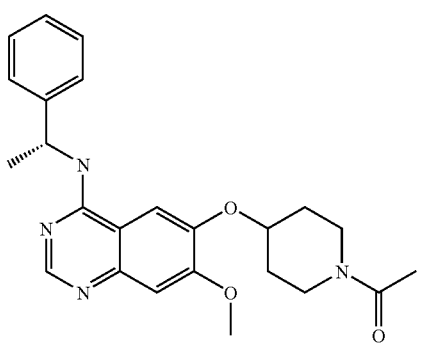

Prepared by treatment of (R)4-(1-phenylethylamino)-6-(piperidin-4-yloxy)-7-methoxy-quinazoline dihydrochloride with acetic anhydride and N-ethyldiisopropylamine in tetrahydrofuran.

$R_f$: 0.19 (silica gel, ethyl acetate/methanol/conc. aqueous ammonia=90:10:1)

Mass spectrum (ESI$^+$): m/z=421 [M+H]$^+$

The following compounds are obtained analogously to Example 4:

(1) (R)-4-(1-Phenylethylamino)-6-(1-methanesulphonylpiperidin-4-yloxy)-7-methoxy-quinazoline

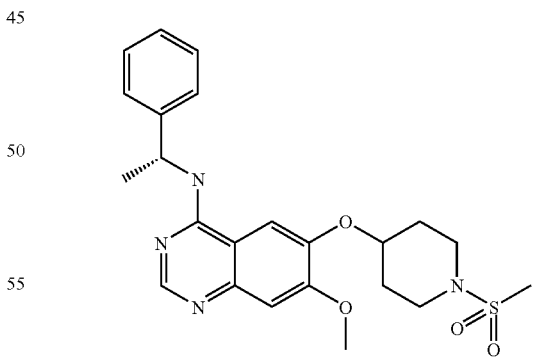

The reaction is carried out using methanesulphonic acid chloride.

$R_f$: 0.48 (silica gel, ethyl acetate/methanol/conc. aqueous ammonia=90:10:1)

Mass spectrum (ESI$^+$): m/z=457 [M+H]$^+$ (2) (R)-4-(1-Phenylethylamino)-6-{1-[(morpholin-4-yl)carbonyl]-piperidin-4-yloxy}-7-methoxyquinazoline

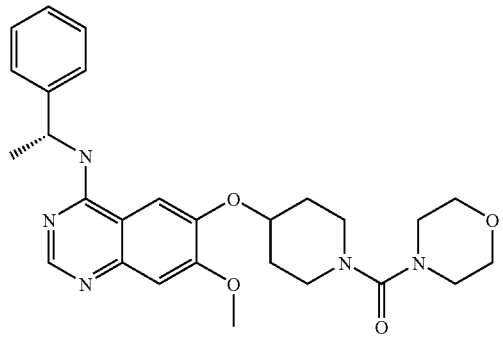

The reaction is carried out using (morpholin-4-yl)carbonyl chloride.

$R_f$: 0.34 (silica gel, ethyl acetate/methanol/conc. aqueous ammonia=90:10:1)

Mass spectrum (ESI$^+$): m/z=492 [M+H]$^+$ (3) (R)-4-(1-Phenylethylamino)-6-(1-cyanopiperidin-4-yloxy)-7-methoxyquinazoline

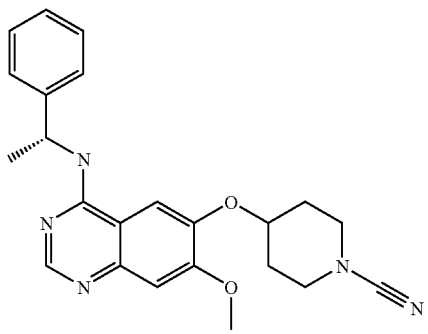

The reaction is carried out using cyanogen bromide in methylene chloride.

$R_f$: 0.54 (silica gel, ethyl acetate/methanol/conc. aqueous ammonia=95:5:1)

Mass spectrum (ESI$^+$): m/z=404 [M+H]$^+$

The following compounds can also be prepared analogously to the abovementioned examples and other processes known from the literature:

| Example No. | Structure |
|---|---|
| (1) | 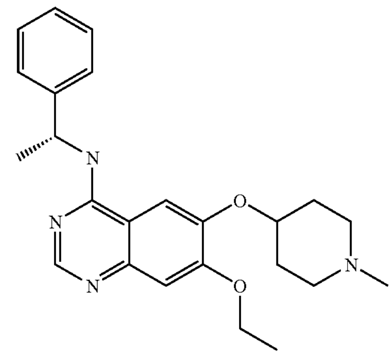 |
| (2) | 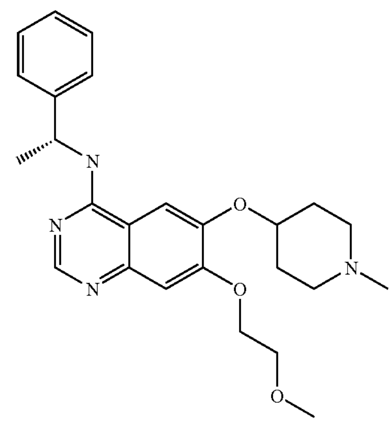 |
| (3) | 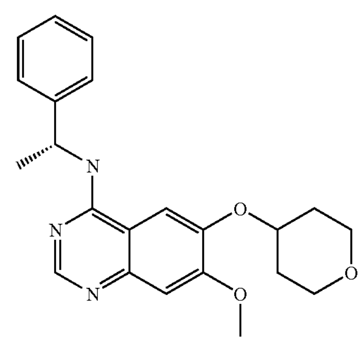 |
| (4) | 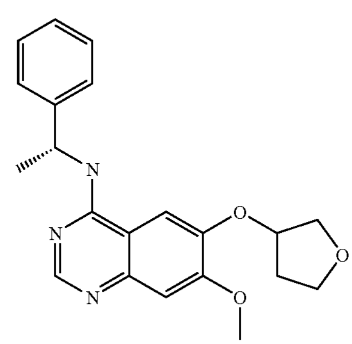 |

| Example No. | Structure |
|---|---|
| (5) | 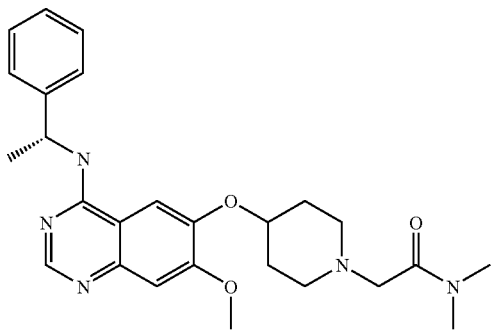 |
| (6) | 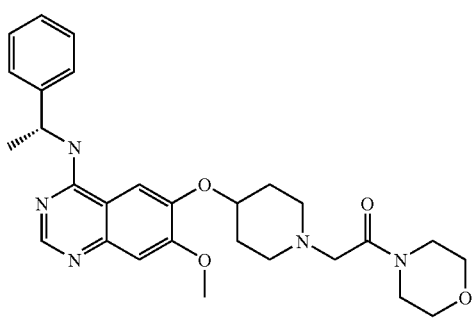 |
| (7) | 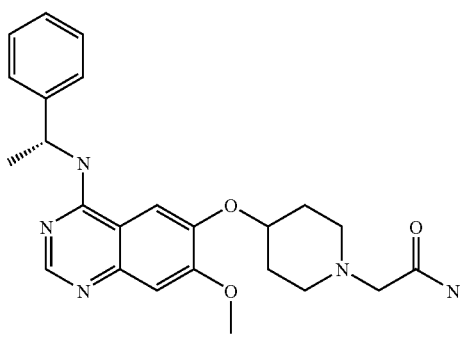 |
| (8) | 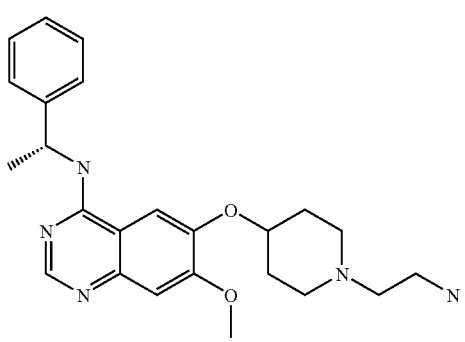 |
| (9) | 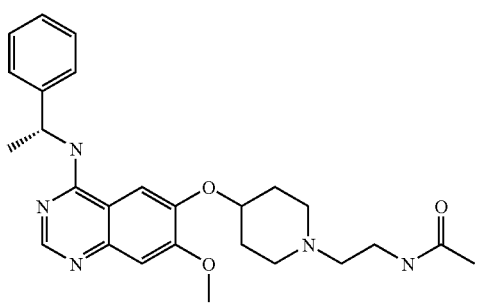 |
| (10) | 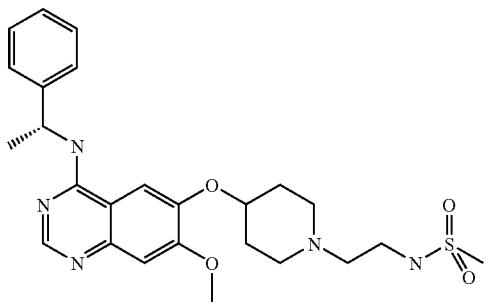 |
| (11) | 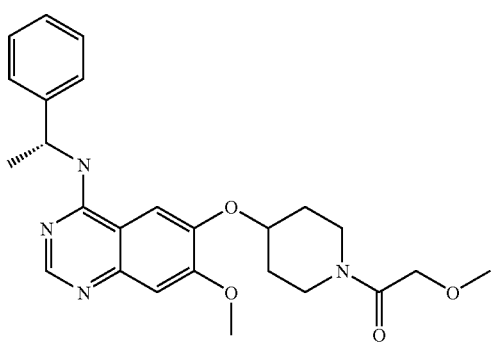 |
| (12) | 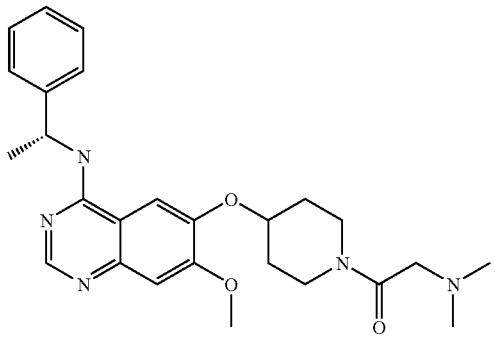 |

-continued
| Example No. | Structure |
|---|---|
| (13) | 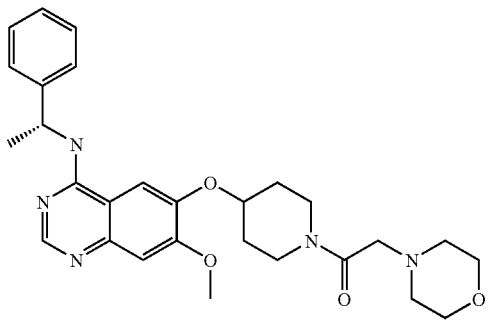 |
| (14) | 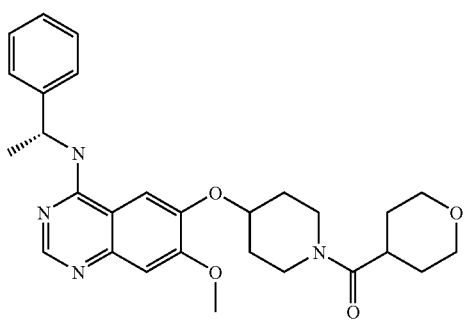 |
| (15) | 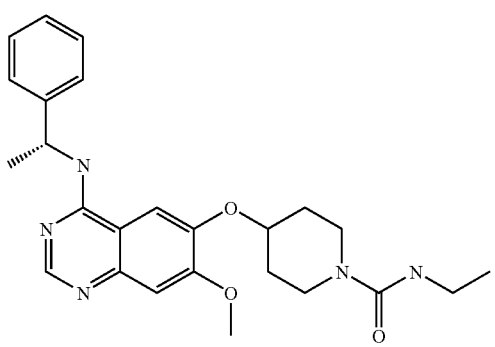 |
| (16) | 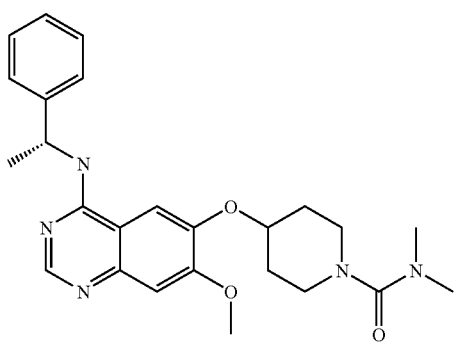 |
-continued
| Example No. | Structure |
|---|---|
| (17) | 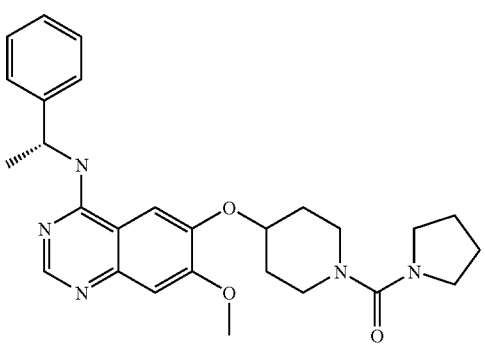 |
| (18) | 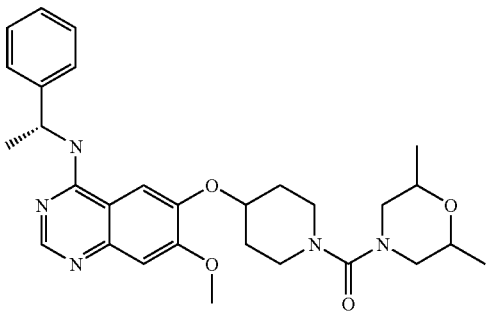 |
| (19) | 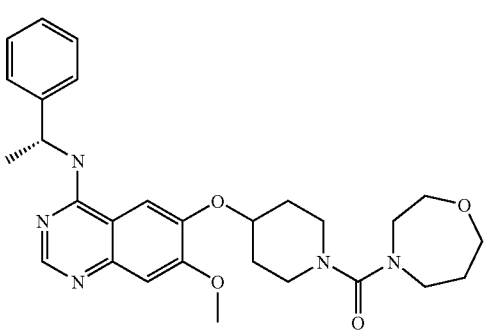 |
| (20) | 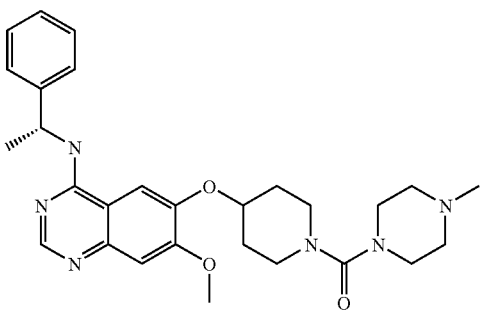 |

-continued
| Example No. | Structure |
|---|---|
| (21) | 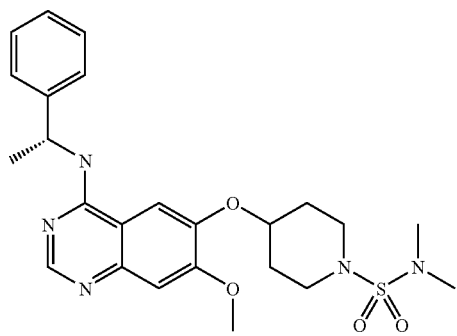 |
| (22) | 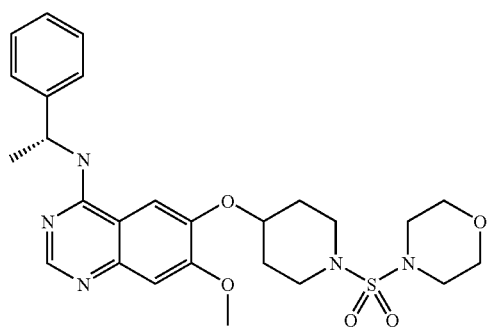 |
| (23) | 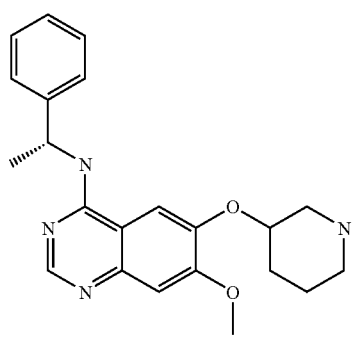 |
| (24) | 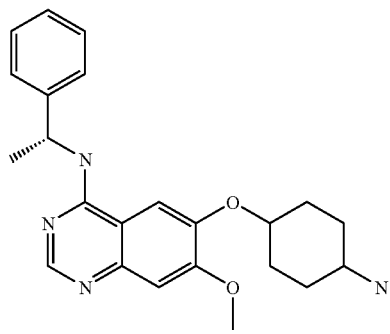 |
-continued
| Example No. | Structure |
|---|---|
| (25) | 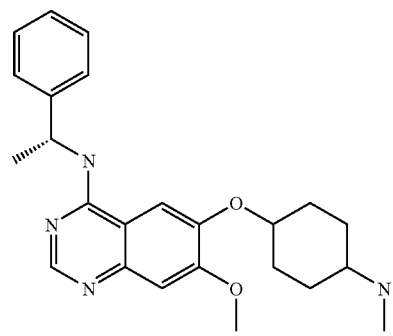 |
| (26) | 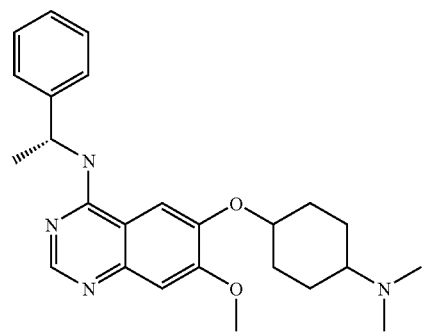 |
| (27) | 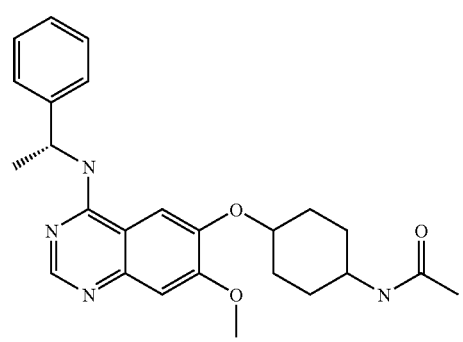 |
| (28) | 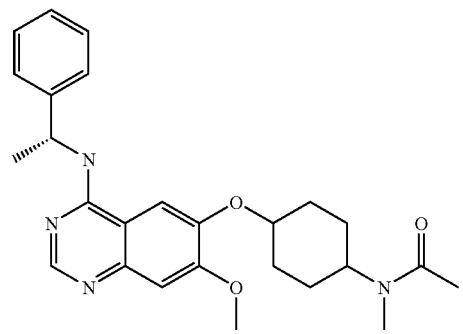 |

-continued

| Example No. | Structure |
|---|---|
| (29) | 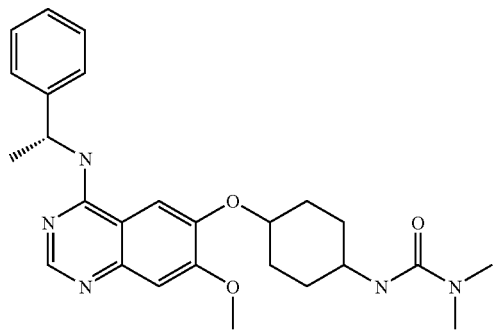 |
| (30) | 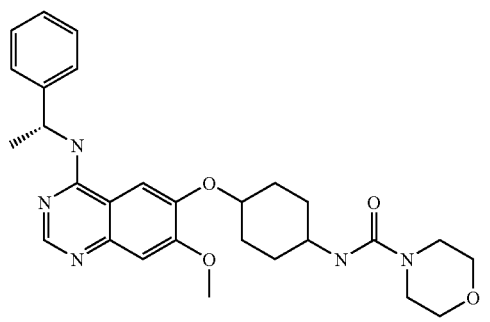 |
| (31) | 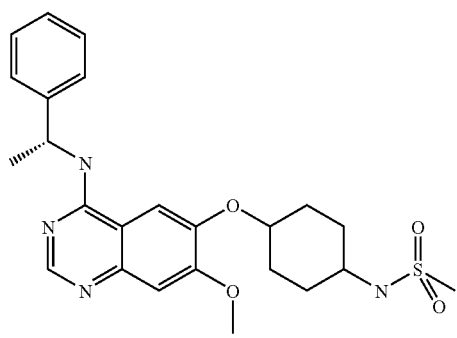 |
| (32) | 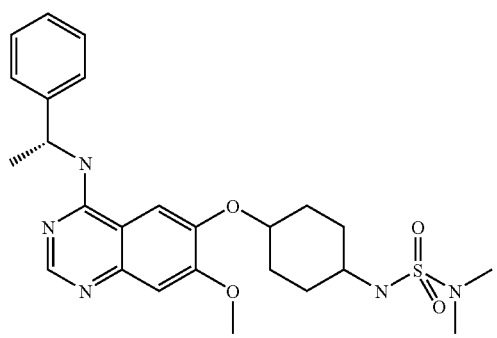 |

-continued

| Example No. | Structure |
|---|---|
| (33) | 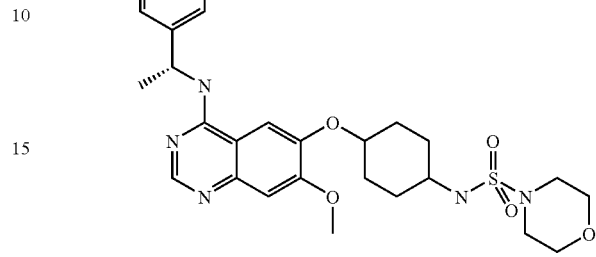 |
| (34) | 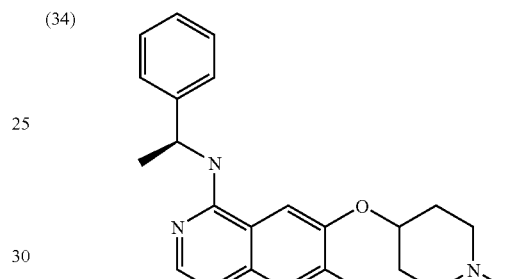 |

EXAMPLE 5

Coated tablets containing 75 mg of active substance

Composition:

1 coated tablet contains:

| | |
|---|---:|
| Active substance | 75.0 mg |
| Calcium phosphate | 93.0 mg |
| Maize starch | 35.5 mg |
| Polyvinylpyrrolidone | 10.0 mg |
| Hydroxypropylmethylcellulose | 15.0 mg |
| Magnesium stearate | 1.5 mg |
| | 230.0 mg |

Preparation:

The active substance is mixed with calcium phosphate, maize starch, polyvinylpyrrolidone, hydroxypropylmethylcellulose and half the stated amount of magnesium stearate. Pressings having a diameter of about 13 mm are prepared on a tabletting machine; these are grated through a sieve having a mesh width of 1.5 mm on a suitable machine and mixed with the remaining amount of magnesium stearate. These granules are pressed on a tabletting machine to give tablets having the desired shape.

| | |
|---|---|
| Core weight: | 230 mg |
| Die: | 9 mm, convex |

The coated tablet cores thus prepared are covered with a film which consists essentially of hydroxypropylmethylcellulose. The finished film-coated tablets are glazed with beeswax.

| | |
|---|---|
| Coated tablet weight: | 245 mg. |

EXAMPLE 6

Tablets containing 100 mg of active substance

Composition:
1 coated tablet contains:

| | |
|---|---|
| Active substance | 100.0 mg |
| Lactose | 80.0 mg |
| Maize starch | 34.0 mg |
| Polyvinylpyrrolidone | 4.0 mg |
| Magnesium stearate | 2.0 mg |
| | 220.0 mg |

Preparation Process:

Active compound, lactose and starch are mixed and uniformly moistened with an aqueous solution of the polyvinylpyrrolidone. After sieving the moist mass (2.0 mm mesh width) and drying in a rack drying oven at 50° C. it is sieved again (1.5 mm mesh width) and the lubricant is admixed. The press-ready mixture is processed to give tablets.

| | |
|---|---|
| Tablet weight: | 220 mg |
| Diameter: | 10 mm, biplanar having a facet on both sides and breaking notch on one side. |

EXAMPLE 7

Tablets containing 150 mg of active substance

Composition:
1 coated tablet contains:

| | |
|---|---|
| Active substance | 150.0 mg |
| Lactose, powdered | 89.0 mg |
| Maize starch | 40.0 mg |
| Colloidal silicic acid | 10.0 mg |
| Polyvinylpyrrolidone | 10.0 mg |
| Magnesium stearate | 1.0 mg |
| | 300.0 mg |

Preparation:

The active substance mixed with lactose, maize starch and silicic acid is moistened with a 20% strength aqueous polyvinylpyrrolidone solution and pounded through a sieve having a mesh width of 1.5 mm.

The granules dried at 45° C. are again grated through the same sieve and mixed with the stated amount of magnesium stearate. Tablets are pressed from the mixture.

| | |
|---|---|
| Tablet weight: | 300 mg |
| Die: | 10 mm, flat |

EXAMPLE 8

Hard gelatine capsules containing 150 mg of active substance

Composition:
1 coated tablet contains:

| | |
|---|---|
| Active compound | 150.0 mg |
| Maize starch, dried about | 180.0 mg |
| Lactose, powdered about | 87.0 mg |
| Magnesium stearate | 3.0 mg |
| about | 420.0 mg |

Preparation:

The active compound is blended with the excipients, passed through a sieve of mesh width 0.75 mm and mixed homogeneously in a suitable apparatus.

The final mixture is filled into hard gelatine capsules of size 1.

Capsule filling: about 320 mg
Capsule shell: hard gelatine capsule size 1.

EXAMPLE 9

Suppositories containing 150 mg of active substance

Composition:
1 coated tablet contains:

| | |
|---|---|
| Active compound | 150.0 mg |
| Polyethylene glycol 1500 | 550.0 mg |
| Polyethylene glycol 6000 | 460.0 mg |
| Polyoxyethylene sorbitan monostearate | 840.0 mg |
| | 2000.0 mg |

Preparation:

After melting the suppository mass, the active compound is dispersed homogeneously therein and the melt is poured into pre-cooled moulds.

EXAMPLE 10

Suspension containing 50 mg of active substance

Composition:
100 ml of suspension contain:

| | |
|---|---|
| Active compound | 1.00 g |
| Carboxymethylcellulose Na salt | 0.10 g |
| Methyl p-hydroxybenzoate | 0.05 g |
| Propyl p-hydroxybenzoate | 0.01 g |

-continued

| Sucrose | 10.00 g |
| --- | --- |
| Glycerol | 5.00 g |
| Sorbitol solution, 70% strength | 20.00 g |
| Flavouring | 0.30 g |
| Water, dist. | to 100.00 ml |

Preparation:

Distilled water is heated to 70° C. Methyl and propyl p-hydroxybenzoate and also glycerol and carboxymethylcellulose sodium salt are dissolved in this with stirring. The mixture is cooled to room temperature and the active compound is added with stirring and homogeneously dispersed. After adding and dissolving the sugar, the sorbitol solution and the flavouring, the suspension is evacuated with stirring for deaeration.

5 ml of suspension contain 50 mg of active compound.

EXAMPLE 11

Ampoules containing 10 mg of active substance

Composition:

| Active compound | 10.0 mg |
| --- | --- |
| 0.01 N hydrochloric acid q.s. | |
| Water, double-distilled | to 2.0 ml |

Preparation:

The active substance is dissolved in the required amount of 0.01 N HCl, rendered isotonic using sodium chloride, sterile-filtered and filled into 2 ml ampoules.

EXAMPLE 12

Ampoules containing 50 mg of active substance

Composition:

| Active compound | 50.0 mg |
| --- | --- |
| 0.01 N hydrochloric acid q.s. | |
| Water, double-distilled | to 10.0 ml |

Preparation:

The active substance is dissolved in the required amount of 0.01 N HCl, rendered isotonic using sodium chloride, sterile-filtered and filled into 10 ml ampoules.

EXAMPLE 13

Capsules for powder inhalation containing 5 mg of active substance 1 capsule contains:

| Active substance | 5.0 mg |
| --- | --- |
| Lactose for inhalation purposes | 15.0 mg |
| | 20.0 mg |

Preparation:

The active substance is mixed with lactose for inhalation purposes. The mixture is filled into capsules on a capsule machine (weight of the empty capsule about 50 mg).

Capsule weight: 70.0 mg

Capsule size: 3

EXAMPLE 14

Inhalation solution for a hand nebulizer containing 2.5 mg of active substance 1 stroke contains:

| Active substance | 2.500 mg |
| --- | --- |
| Benzalkonium chloride | 0.001 mg |
| 1N hydrochloric acid q.s. | |
| Ethanol/water (50/50) | to 15.000 mg |

Preparation:

The active substance and benzalkonium chloride are dissolved in ethanol/water (50/50). The pH of the solution is adjusted using 1N hydrochloric acid. The adjusted solution is filtered and filled into containers (cartridges) suitable for the hand nebulizer.

Filling mass of the container: 4.5 g

What is claimed is:

1. A compound of the formula

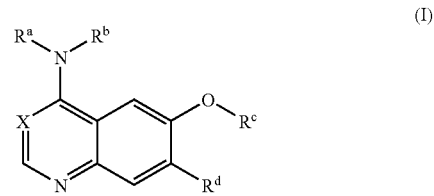

(I)

in which $R^a$ is a hydrogen atom or a $C_{1-4}$-alkyl group, $R^b$ is a 1-phenylethyl group, in which the phenyl nucleus is substituted by groups $R^1$ to $R^3$, where $R^1$ and $R^2$, which can be identical or different, are in each case a hydrogen, fluorine, chlorine, bromine or iodine atom, a $C_{1-4}$-alkyl, hydroxyl, $C_{1-4}$-alkoxy, $C_{2-3}$-alkenyl or $C_{2-3}$-alkynyl group, an aryl, aryloxy, arylmethyl or arylmethoxy group, a heteroaryl, heteroaryloxy, heteroarylmethyl or heteroarylmethoxy group, a methyl or methoxy group substituted by 1 to 3 fluorine atoms or a cyano, nitro or amino group, and $R^3$ is a hydrogen, fluorine, chlorine or bromine atom or a methyl or trifluoromethyl group, $R^c$ is a cyclobutyl, cyclopentyl or cyclohexyl group, which is in each case substituted by a group $R^4$—N—$R^5$, where $R^4$ is a hydrogen atom or a $C_{1-3}$-alkyl group and $R^5$ is a hydrogen atom or a $C_{1-3}$-alkyl group, an aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, pyrrolidin-1-ylcarbonyl-$C_{1-3}$-alkyl, piperidin-1-ylcarbonyl-$C_{1-3}$-alkyl, homopiperidin-1-ylcarbonyl-$C_{1-3}$-alkyl, morpholin-4-ylcarbonyl-$C_{1-3}$-alkyl, homomorpholin-4-ylcarbonyl-$C_{1-3}$-alkyl, piperazin-1-ylcarbonyl-$C_{1-3}$-alkyl, 4-$C_{1-3}$-alkylpiperazin-1-ylcarbonyl-$C_{1-3}$-alkyl, homopiperazin-1-ylcarbonyl-$C_{1-3}$-alkyl or a 4-$C_{1-3}$-alkylhomopiperazin-1-ylcarbonyl-$C_{1-3}$-alkyl group, a hydroxy-$C_{2-4}$-alkyl, $C_{1-3}$-alkyloxy-$C_{2-4}$-alkyl, $C_{1-4}$-alkyloxycarbonylamino-$C_{2-4}$-alkyl, amino-$C_{2-4}$-alkyl, $C_{1-3}$-alkylamino-$C_{2-4}$-alkyl, di-($C_{1-3}$-alkyl)amino-$C_{2-4}$-alkyl, $C_{1-3}$-alkylcarbonylamino-$C_{2-4}$-alkyl, aminocarbonylamino-$C_{2-4}$-alkyl, $C_{1-3}$-alkylaminocarbonylamino-$C_{2-4}$-alkyl, di-($C_{1-3}$-alkyl)aminocarbonylamino-$C_{2-4}$-alkyl, pyrrolidin-1-ylcarbonylamino-$C_{2-4}$-alkyl, piperidin-1-ylcarbonylamino-$C_{2-4}$-alkyl, morpholin-4-ylcarbonylamino-$C_{2-4}$-alkyl, $C_{1-3}$-alkylsulphonyl-$C_{2-4}$-alkyl or a $C_{1-3}$-alkylsulphonylamino-$C_{2-4}$-alkyl group, a (2-oxopyrrolidin-1-yl)-$C_{2-4}$-alkyl, (2-oxopiperidin-1-yl)-$C_{2-4}$-alkyl, (3-oxo-morpholin-4-yl)-$C_{2-4}$-alkyl, (2-oxoimidazolidin-1-yl)-$C_{2-4}$-alkyl, (2-oxo-3-$C_{1-3}$-alkyl-imidazolidin-1-yl)-$C_{2-4}$-alkyl, (2-oxohexahydropyrimidin-1-yl)-$C_{2-4}$-alkyl or a (2-oxo-3-$C_{1-3}$-alkylhexahydropyrimidin-1-yl)-$C_{2-4}$-alkyl group, a $C_{1-4}$-alkylsulphonyl, chloro-$C_{1-4}$-alkylsulphonyl, bromo-$C_{1-4}$-alkylsulphonyl, amino-$C_{1-4}$-alkylsulphonyl, $C_{1-3}$-alkylamino-$C_{1-4}$-alkylsulphonyl, di-($C_{1-3}$-alkyl)-amino-$C_{1-4}$-alkylsulphonyl, (pyrrolidin-1-yl)-$C_{1-4}$-alkylsulphonyl, (piperidin-1-yl)-$C_{1-4}$-alkylsulphonyl, (homopiperidin-1-yl)-$C_{1-4}$-alkylsulphonyl, (morpholin-4-yl)-$C_{1-4}$-alkylsulphonyl, (homomorpholin-4-yl)-$C_{1-4}$-alkylsulphonyl, (piperazin-1-yl)-$C_{1-4}$-alkylsulphonyl, (4-$C_{1-3}$-alkylpiperazin-1-yl)-$C_{1-4}$-alkylsulphonyl, (homo-piperazin-1-yl)-$C_{1-4}$-alkylsulphonyl or a (4-$C_{1-3}$-alkylhomopiperazin-1-yl)-$C_{1-4}$-alkylsulphonyl group, a $C_{1-4}$-alkyloxycarbonyl group, a formyl, $C_{1-4}$-alkylcarbonyl, $C_{1-3}$-alkyloxy-$C_{1-4}$-alkylcarbonyl, tetrahydrofuranyl-carbonyl, tetrahydropyranylcarbonyl, amino-$C_{1-4}$-alkylcarbonyl, $C_{1-3}$-alkylamino-$C_{1-4}$-alkylcarbonyl, di-($C_{1-3}$-alkyl)amino-$C_{1-4}$-alkylcarbonyl, pyrrolidin-1-yl-$C_{1-4}$-alkylcarbonyl, piperidin-1-yl-$C_{1-4}$-alkylcarbonyl, (homopiperidin-1-yl)-$C_{1-4}$-alkylcarbonyl, morpholin-4-yl-$C_{1-4}$-alkylcarbonyl, (homomorpholin-4-yl)-$C_{1-4}$-alkylcarbonyl, (piperazin-1-yl)-$C_{1-4}$-alkylcarbonyl, (4-$C_{1-3}$-alkylpiperazin-1-yl)-$C_{1-4}$-alkylcarbonyl, (homopiperazin-1-yl)-$C_{1-4}$-alkylcarbonyl, (4-$C_{1-3}$-alkyl-homopiperazin-1-yl)-$C_{1-4}$-alkylcarbonyl or a $C_{1-3}$-alkylsulphonyl-$C_{1-4}$-alkylcarbonyl group, a cyano, aminocarbonyl, $C_{1-3}$-alkylaminocarbonyl, di-($C_{1-3}$-alkyl)aminocarbonyl, ($C_{1-3}$-alkyloxy-$C_{2-4}$-alkyl)aminocarbonyl, N—($C_{1-3}$-alkyl)-N—($C_{1-3}$-alkyloxy-$C_{2-4}$-alkyl)-aminocarbonyl, arylaminocarbonyl, pyrrolidin-1-ylcarbonyl, piperidin-1-ylcarbonyl, homopiperidin-1-ylcarbonyl, morpholin-4-ylcarbonyl, homomorpholin-4-yl-carbonyl, 2-oxa-5-azabicyclo[2.2.1]hept-5-ylcarbonyl, 3-oxa-8-azabicyclo[3.2.1]oct-8-ylcarbonyl, 8-oxa-3-azabicyclo[3.2.1]oct-3-ylcarbonyl, piperazin-1-yl-carbonyl, 4-$C_{1-3}$-alkylpiperazin-1-ylcarbonyl, homopiperazin-1-ylcarbonyl, 4-$C_{1-3}$-alkylhomopiperazin-1-ylcarbonyl, aminosulphonyl, $C_{1-3}$-alkylaminosulphonyl, di-($C_{1-3}$-alkyl)aminosulphonyl, pyrrolidin-1-yl-sulphonyl, piperidin-1-ylsulphonyl, homopiperidin-1-ylsulphonyl, morpholin-4-ylsulphonyl, homomorpholin-4-yl-sulphonyl, piperazin-1-ylsulphonyl, 4-$C_{1-3}$-alkylpiperazin-1-ylsulphonyl, homo-piperazin-1-ylsulphonyl or a 4-$C_{1-3}$-alkylhomopiperazin-1-ylsulphonyl group, a cyclobutyl, cyclopentyl or cyclohexyl group, which is in each case substituted by a group $R^6$, where
  $R^6$ is a 2-oxopyrrolidin-1-yl, 2-oxopiperidin-1-yl, 3-oxomorpholin-4-yl, 2-oxo-imidazolidin-1-yl, 2-oxo-3-$C_{1-3}$-alkylimidazolidin-1-yl, 2-oxohexahydropyrimidin-1-yl or a 2-oxo-3-$C_{1-3}$-alkylhexahydropyrimidin-1-yl group, an azetidin-3-yl group, which is substituted in the 1-position by the group $R^5$, where $R^5$ is defined as mentioned above, a pyrrolidin-3-yl group, which is substituted in the 1-position by the group $R^5$, where $R^5$ is defined as mentioned above, a piperidin-3-yl group, which is substituted in the 1-position by the group $R^5$, where $R^5$ is defined as mentioned above, a piperidin-4-yl group, which is substituted in the 1-position by the group $R^5$, where $R^5$ is defined as mentioned above, or a tetrahydrofuran-3-yl, tetrahydropyran-3-yl or tetrahydropyran-4-yl group, $R^d$ is a hydrogen atom or a fluorine, chlorine or bromine atom, a hydroxyl group, a $C_{1-4}$-alkyloxy group, a methoxy group substituted by 1 to 3 fluorine atoms, an ethyloxy group substituted by 1 to 5 fluorine atoms, a $C_{2-4}$-alkyloxy group, which is substituted by the group $R^6$ or $R^7$, where
  $R^6$ is defined as mentioned above and
  $R^7$ is a hydroxyl, $C_{1-3}$-alkyloxy, $C_{3-6}$-cycloalkyloxy, amino, $C_{1-3}$-alkylamino, di-($C_{1-3}$-alkyl)amino, bis(2-methoxyethyl)amino, pyrrolidin-1-yl, piperidin-1-yl, homopiperidin-1-yl, morpholin-4-yl, homomorpholin-4-yl, 2-oxa-5-azabicyclo-[2.2.1]hept-5-yl, 3-oxa-8-azabicyclo[3.2.1]oct-8-yl, 8-oxa-3-azabicyclo[3.2.1]oct-3-yl, piperazin-1-yl, 4-$C_{1-3}$-alkylpiperazin-1-yl, homopiperazin-1-yl or $C_{1-3}$-alkyl-homopiperazin-1-yl group, or
  a formylamino, $C_{1-4}$-alkylcarbonylamino, $C_{1-3}$-alkyloxy-$C_{1-3}$-alkylcarbonylamino, $C_{1-4}$-alkyloxycarbonylamino, aminocarbonylamino, $C_{1-3}$-alkylaminocarbonylamino, di-($C_{1-3}$-alkyl)aminocarbonylamino, pyrrolidin-1-ylcarbonylamino, piperidin-1-yl-carbonylamino, piperazin-1-ylcarbonylamino, 4-$C_{1-3}$-alkylpiperazin-1-ylcarbonyl-amino, morpholin-4-ylcarbonylamino or a $C_{1-4}$-alkylsulphonylamino group, a $C_{3-7}$-cycloalkyloxy or $C_{3-7}$-cycloalkyl-$C_{1-4}$-alkyloxy group, a tetrahydrofuran-3-yloxy, tetrahydropyran-3-yloxy or tetrahydropyran-4-yloxy group, a tetrahydrofuranyl-$C_{1-4}$-alkyloxy or tetrahydropyranyl-$C_{1-4}$-alkyloxy group, a $C_{1-4}$-alkoxy group, which is substituted by a pyrrolidinyl, piperidinyl or homopiperidinyl group substituted in the 1-position by the group $R^8$, where
  $R^8$ is a hydrogen atom or a $C_{1-3}$-alkyl group, or a $C_{1-4}$-alkoxy group, which is substituted by a morpholinyl group substituted in the 4-position by the group $R^8$, where $R^8$ is defined as mentioned above, and X is a nitrogen atom, and where the aryl groups mentioned in the definition of the abovementioned groups are in each case to be understood as meaning a phenyl group which is mono- or disubstituted by $R^9$, where the substituents can be identical or different and $R^9$ is a hydrogen atom, a fluorine, chlorine, bromine, or iodine atom or a $C_{1-3}$-alkyl, hydroxyl, $C_{1-3}$-alkyloxy, difluoromethyl, trifluoromethyl, difluoromethoxy, trifluoromethoxy or cyano group, the heteroaryl groups mentioned in the definition of the abovementioned groups are to be understood as meaning a pyridyl, pyridazinyl, pyrimidinyl or pyrazinyl group, where the abovementioned heteroaryl groups are in each case mono- or disubstituted by the group $R^9$, where the substituents can be identical or different and $R^9$ is defined as mentioned above, and the abovementioned pyrrolidinyl, piperidinyl, piperazinyl and morpholinyl groups can in each case be substituted by one or two $C_{1-3}$-alkyl groups, and if not mentioned otherwise, the abovementioned alkyl groups can be straight-chain or branched, or a tautomer or salt thereof.

2. A compound in accordance with claim 1, in which $R^a$ is a hydrogen atom, $R^b$ is a 1-phenylethyl group, $R^c$ is a cyclopentyl group, which is substituted in the 3-position by a group $R^4$—N—$R^5$, where $R^4$ is a hydrogen atom or a $C_{1-3}$-alkyl group and
$R^5$ is a hydrogen atom or a $C_{1-3}$-alkyl group, an aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, pyrrolidin-1-ylcarbonyl-$C_{1-3}$-alkyl, piperidin-1-ylcarbonyl-$C_{1-3}$-alkyl, piperazin-1-ylcarbonyl-$C_{1-3}$-alkyl, 4-$C_{1-3}$-alkylpiperazin-1-ylcarbonyl-$C_{1-3}$-alkyl or morpholin-4-ylcarbonyl-$C_{1-3}$-alkyl group, a hydroxy-$C_{2-4}$-alkyl, $C_{1-3}$-alkyloxy-$C_{2-4}$-alkyl, $C_{1-4}$-alkyloxycarbonylamino-$C_{2-4}$-alkyl, amino-$C_{2-4}$-alkyl, $C_{1-3}$-alkylamino-$C_{2-4}$-alkyl, di-($C_{1-3}$-alkyl)amino-$C_{2-4}$-alkyl, $C_{1-3}$-alkylcarbonylamino-$C_{2-4}$-alkyl, aminocarbonylamino-$C_{2-4}$-alkyl, $C_{1-3}$-alkylaminocarbonylamino-$C_{2-4}$-alkyl, di-($C_{1-3}$-alkyl)aminocarbonylamino-$C_{2-4}$-alkyl, morpholin-4-ylcarbonylamino-$C_2$-4-alkyl, $C_{1-3}$-alkylsulphonyl-$C_{2-4}$-alkyl or $C_{1-3}$-alkylsulphonylamino-$C_{2-4}$-alkyl group, a (2-oxopyrrolidin-1-yl)-$C_{2-4}$-alkyl, (2-oxopiperidin-1-yl)-$C_{2-4}$-alkyl, (3-oxo-morpholin-4-yl)-$C_{2-4}$-alkyl, (2-oxoimidazolidin-1-yl)-$C_{2-4}$-alkyl, (2-oxo-3-methyl-imidazolidin-1-yl)-$C_{2-4}$-alkyl, (2-oxohexahydropyrimidin-1-yl)-$C_{2-4}$-alkyl or (2-oxo-3-methylhexahydropyrimidin-1-yl)-$C_{2-4}$-alkyl group, a $C_{1-3}$-alkylsulphonyl, chloro-$C_{2-4}$-alkylsulphonyl, bromo-$C_{2-4}$-alkylsulphonyl, amino-$C_{2-4}$-alkylsulphonyl, $C_{1-3}$-alkylamino-$C_{2-4}$-alkylsulphonyl, di-($C_{1-3}$-alkyl)-amino-$C_{2-4}$-alkylsulphonyl, (pyrrolidin-1-yl)-$C_{2-4}$-alkylsulphonyl, (piperidin-1-yl)-$C_{2-4}$-alkylsulphonyl or (morpholin-4-yl)-$C_{2-4}$-alkylsulphonyl group, a $C_{1-4}$-alkyloxycarbonyl group, a formyl, $C_{1-3}$-alkylcarbonyl, $C_{1-3}$-alkyloxy-$C_{1-3}$-alkylcarbonyl, tetrahydrofuranyl-carbonyl, tetrahydropyranylcarbonyl, amino-$C_{1-3}$-alkylcarbonyl, $C_{1-3}$-alkylamino-$C_{1-3}$-alkylcarbonyl, di-($C_{1-3}$-alkyl)amino-$C_{1-3}$-alkylcarbonyl, pyrrolidin-1-yl-$C_{1-3}$-alkylcarbonyl, piperidin-1-yl-$C_{1-3}$-alkylcarbonyl, piperazin-1-yl-$C_{1-3}$-alkyl-carbonyl, 4-$C_{1-3}$-alkylpiperazin-1-yl-$C_{1-3}$-alkylcarbonyl, morpholin-4-yl-$C_{1-3}$-alkylcarbonyl or a $C_{1-3}$-alkylsulphonyl-$C_{1-3}$-alkylcarbonyl group, a cyano, aminocarbonyl, $C_{1-3}$-alkylaminocarbonyl, di-($C_{1-3}$-alkyl)aminocarbonyl, ($C_{1-3}$-alkyloxy-$C_{2-4}$-alkyl)aminocarbonyl, N—($C_{1-3}$-alkyl)-N—($C_{1-3}$-alkyloxy-$C_{2-4}$-alkyl)-aminocarbonyl, phenylaminocarbonyl, pyrrolidin-1-ylcarbonyl, piperidin-1-yl-carbonyl, morpholin-4-ylcarbonyl, $C_{1-3}$-alkylmorpholin-4-ylcarbonyl, di-($C_{1-3}$-alkyl)morpholin-4-ylcarbonyl, homomorpholin-4-ylcarbonyl, 2-oxa-5-azabicyclo-[2.2.1]hept-5-ylcarbonyl, 3-oxa-8-azabicyclo[3.2.1]oct-8-ylcarbonyl, 8-oxa-3-azabicyclo[3.2.1]oct-3-ylcarbonyl, piperazin-1-ylcarbonyl, 4-($C_{1-3}$-alkyl)-piperazin-1-ylcarbonyl, aminosulphonyl, $C_{1-3}$-alkylaminosulphonyl, di-($C_{1-3}$-alkyl)amino-sulphonyl, pyrrolidin-1-yl-sulphonyl, piperidin-1-ylsulphonyl or a morpholin-4-ylsulphonyl group, or a cyclopentyl group, which is substituted in the 3-position by a group $R^6$, where $R^6$ is a 2-oxopyrrolidin-1-yl, 2-oxopiperidin-1-yl, 3-oxomorpholin-4-yl, 2-oxo-imidazolidin-1-yl, 2-oxo-3-methylimidazolidin-1-yl, 2-oxohexahydropyrimidin-1-yl or a 2-oxo-3-methylhexahydropyrimidin-1-yl group, a cyclohexyl group, which is substituted in the 3-position or in the 4-position by a group $R^4$—N—$R^5$, where $R^4$ and $R^5$ are defined as mentioned above, a cyclohexyl group, which is substituted in the 3-position or in the 4-position by a group $R^6$, where $R^6$ is defined as mentioned above, a pyrrolidin-3-yl group, which is substituted in the 1-position by the group $R^5$, where $R^5$ is defined as mentioned above, a piperidin-3-yl group, which is substituted in the 1-position by the group $R^5$, where $R^5$ is defined as mentioned above, a piperidin-4-yl group, which is substituted in the 1-position by the group $R^5$, where $R^5$ is defined as mentioned above, or a tetrahydrofuran-3-yl, tetrahydropyran-3-yl or tetrahydropyran-4-yl group, $R^d$ is a hydrogen atom, a $C_{1-3}$-alkyloxy group, a methoxy group, which is substituted by one to three fluorine atoms, an ethyloxy group, which is substituted in the 2-position by a group $R^6$ or $R^7$, where $R^6$ is defined as mentioned above and $R^7$ is a hydroxyl, $C_{1-3}$-alkyloxy, amino, $C_{1-3}$-alkylamino, di-($C_{1-3}$-alkyl)amino, bis(2-methoxyethyl)amino, pyrrolidin-1-yl, piperidin-1-yl, morpholin-4-yl, homomorpholin-4-yl, 2-oxa-5-azabicyclo[2.2.1]hept-5-yl, 3-oxa-8-azabicyclo[3.2.1]oct-8-yl, 8-oxa-3-azabicyclo[3.2.1]oct-3-yl, piperazin-1-yl or a 4-$C_{1-3}$-alkylpiperazin-1-yl group, or a formylamino, $C_{1-4}$-alkylcarbonylamino, $C_{1-3}$-alkyloxy-$C_{1-3}$-alkylcarbonylamino, $C_{1-4}$-alkyloxycarbonylamino, aminocarbonylamino, $C_{1-3}$-alkylaminocarbonylamino, di-($C_{1-3}$-alkyl)aminocarbonylamino, pyrrolidin-1-ylcarbonylamino, piperidin-1-ylcarbonylamino, piperazin-1-ylcarbonylamino, 4-$C_{1-3}$-alkylpiperazin-1-ylcarbonylamino, morpholin-4-ylcarbonylamino or a $C_{1-4}$-alkylsulphonylamino group, a propyloxy group, which is substituted in the 3-position by a group $R^6$ or $R^7$, where $R^6$ and $R^7$ are defined as mentioned above, or a butyloxy group, which is substituted in the 4-position by a group $R^6$ or $R^7$, where $R^6$ and $R^7$ are defined as mentioned above, and X is a nitrogen atom, where, if not mentioned otherwise, the abovementioned alkyl groups can be straight-chain or branched, or a tautomer or salt thereof.

3. A compound in accordance with claim 1, in which
$R^a$ is a hydrogen atom,
$R^b$ is a 1-phenylethyl group,
$R^c$ is a cyclohexyl group, which is substituted in the 3-position or in the 4-position by a group $R^4$—N—$R^5$, where
$R^4$ is a hydrogen atom, a methyl or ethyl group and
$R^5$ is a hydrogen atom, a methyl, aminocarbonylmethyl, methylaminocarbonylmethyl, dimethylaminocarbonylmethyl, pyrrolidin-1-ylcarbonylmethyl, piperidin-1-ylcarbonylmethyl, piperazin-1-ylcarbonylmethyl, 4-methylpiperazin-1-ylcarbonyl methyl, morpholin-4-ylcarbonylmethyl, 2-(morpholin-4-yl-carbonyl)ethyl or 3-(morpholin-4-yl-carbonyl)propyl group, an ethyl, propyl, 2-hydroxyethyl, 3-hydroxypropyl, 2-methoxyethyl, 3-methoxy-propyl, 2-(butyloxycarbonylamino)ethyl, 2-aminoethyl, 3-aminopropyl, 2-(acetyl-amino)ethyl, 3-(acetylamino)propyl, 2-(ethylcarbonylamino)ethyl, 3-(ethyl-carbonylamino)propyl, 2-(propylcarbonylamino)ethyl, 3-(propylcarbonylamino)-propyl, 2-(ethylaminocarbonylamino)ethyl, 3-(ethylaminocarbonylamino)propyl, 2-(dimethylaminocarbonylamino)ethyl, 3-(dimethylaminocarbonylamino)propyl, 2-(morpholin-4-ylcarbonylamino)ethyl, 3-(morpholin-4-ylcarbonylamino)propyl, 2-(methylsulphonyl)ethyl, 3-(methylsulphonyl)propyl, 2-(methylsulphonylamino)-ethyl or a 3-(methylsulphonylamino)propyl group, a 2-(2-oxopyrrolidin-1-yl)ethyl, 2-(2-oxopiperidin-1-yl)ethyl, 2-(3-oxomorpholin-4-yl)ethyl, 2-(2-oxoimidazolidin-1-yl)ethyl, 2-(2-oxo-3-methylimidazolidin-1-yl)ethyl, 2-(2-oxohexahydropyrimidin-1-yl)ethyl or a 2-(2-oxo-3-methylhexahydropyrimidin-1-yl)ethyl group, a 3-(2-oxopyrrolidin-1-yl)propyl, 3-(2-oxopiperidin-1-yl)propyl, 3-(3-oxomorpholin-4-yl)propyl, 3-(2-oxoimidazolidin-1-yl)propyl, 3-(2-oxo-3-methylimidazolidin-1-yl)propyl, 3-(2-oxohexahydropyrimidin-1-yl)propyl or a 3-(2-oxo-3-methylhexahydropyrimidin-1-yl)propyl group, a methylsulphonyl, ethylsulphonyl, 3-chloropropylsulphonyl, 2-(morpholin-4-yl)-ethylsulphonyl or a 3-(morpholin-4-yl)-propylsulphonyl group, a propyloxycarbonyl or butyloxycarbonyl group, a formyl, acetyl, ethylcarbonyl, propylcarbonyl, methoxyacetyl, (2-methoxy-ethyl)carbonyl, (3-methoxypropyl)carbonyl, tetrahydrofuran-2-ylcarbonyl, tetrahydropyran-4-ylcarbonyl, aminoacetyl, methylaminoacetyl, dimethylamino-acetyl, morpholin-4-ylacetyl, [2-(morpholin-4-yl)ethyl]carbonyl, [3-(morpholin-4-yl)propyl]carbonyl or a methylsulphonylacetyl group, a cyano, aminocarbonyl, methylaminocarbonyl, dimethylaminocarbonyl, ethyl-aminocarbonyl, diethylaminocarbonyl, propylaminocarbonyl, (2-methoxyethyl)-aminocarbonyl, N-methyl-N-(2-methoxyethyl)aminocarbonyl, (3-methoxypropyl)-aminocarbonyl, N-methyl-N-(3-methoxypropyl)aminocarbonyl, phenylamino-carbonyl, pyrrolidin-1-ylcarbonyl, piperidin-1-ylcarbonyl, morpholin-4-ylcarbonyl, 2-methylmorpholin-4-ylcarbonyl, 2,6-dimethylmorpholin-4-ylcarbonyl, homo-morpholin-4-ylcarbonyl, 2-oxa-5-azabicyclo[2.2.1]hept-5-ylcarbonyl, 3-oxa-8-azabicyclo[3.2.1]oct-8-ylcarbonyl, 8-oxa-3-azabicyclo[3.2.1]oct-3-ylcarbonyl, 4-methylpiperazin-1-ylcarbonyl, aminosulphonyl, methylaminosulphonyl, dimethylaminosulphonyl or a morpholin-4-ylsulphonyl group, a cyclohexyl group, which is substituted in the 3-position or in the 4-position by a group $R^6$, where
$R^6$ is a 2-oxopyrrolidin-1-yl, 2-oxopiperidin-1-yl, 3-oxomorpholin-4-yl, 2-oxo-imidazolidin-1-yl, 2-oxo-3-methylimidazolidin-1-yl, 2-oxohexahydropyrimidin-1-yl or a 2-oxo-3-methylhexahydropyrimidin-1-yl group, a pyrrolidin-3-yl group, which is substituted in the 1-position by the group $R^5$, where $R^5$ is defined as mentioned above, a piperidin-3-yl group, which is substituted in the 1-position by the group $R^5$, where $R^5$ is defined as mentioned above, a piperidin-4-yl group, which is substituted in the 1-position by the group $R^5$, where $R^5$ is defined as mentioned above, a tetrahydrofuran-3-yl, tetrahydropyran-3-yl or tetrahydropyran-4-yl group, $R^d$ is a hydrogen atom, a methoxy, difluoromethoxy or ethyloxy group, an ethyloxy group, which is substituted in the 2-position by a group $R^6$ or $R^7$, where $R^6$ is defined as mentioned above and
$R^7$ is a hydroxyl, methoxy, ethoxy, amino, dimethylamino, diethylamino, bis(2-methoxyethyl)amino, pyrrolidin-1-yl, piperidin-1-yl, morpholin-4-yl, homomorpholin-4-yl, 2-oxa-5-azabicyclo[2.2.1]hept-5-yl, 3-oxa-8-azabicyclo[3.2.1]oct-8-yl, 8-oxa-3-azabicyclo[3.2.1]oct-3-yl, piperazin-1-yl, 4-methylpiperazin-1-yl or 4-ethylpiperazin-1-yl group, or an acetylamino, ethylcarbonylamino, propylcarbonylamino, butylcarbonylamino, methoxyacetylamino, butyloxycarbonylamino, ethylaminocarbonylamino, dimethylaminocarbonylamino, pyrrolidin-1-ylcarbonylamino, piperidin-1-ylcarbonylamino, morpholin-4-ylcarbonylamino, methylsulphonylamino, ethylsulphonylamino or butylsulphonylamino group, a propyloxy group, which is substituted in the 3-position by a group $R^6$ or $R^7$, where $R^6$ and $R^7$ are defined as mentioned above, or a butyloxy group, which is substituted in the 4-position by a group $R^6$ or $R^7$, where $R^6$ and $R^7$ are defined as mentioned above, and X is a nitrogen atom, where, if not mentioned otherwise, the abovementioned alkyl groups can be straight-chain or branched, or a tautomer or salt thereof.

4. A compound in accordance with claim 1, in which
$R^a$ is a hydrogen atom,
$R^b$ is a 1-phenylethyl group,
$R^c$ is a cyclohexyl group, which is substituted in the 4-position by an amino, methylamino, dimethylamino, acetylamino, N-(acetyl)methylamino, methoxy-acetylamino, N-(methoxyacetyl)methylamino, tetrahydropyran-4-ylcarbonylamino, N-(tetrahydropyran-4-ylcarbonyl)methylamino, tert-butyloxycarbonylamino, N-(tert-butyloxycarbonyl)methylamino, N-(ethylaminocarbonyl)methylamino, dimethylaminocarbonylamino, N-(dimethylaminocarbonyl)methylamino, N-(piperidin-1-ylcarbonyl)-methylamino, morpholin-4-ylcarbonylamino, N-(morpholin-4-ylcarbonyl)methylamino, N-(4-methylpiperazin-1-ylcarbonyl)methylamino, methylsulphonylamino, N-(methyl-sulphonyl)methylamino, ethylsulphonylamino, N-(ethylsulphonyl)methylamino, dimethylaminosulphonylamino, N-(dimethylaminosulphonyl)methylamino, morpholin-4-yl-sulphonylamino or N-(morpholin-4-ylsulphonyl)methylamino group, a pyrrolidin-3-yl group, a pyrrolidin-3-yl group, which is substituted in the 1-position by a tert-butyloxycarbonyl or methylsulphonyl group, a piperidin-3-yl group, a piperidin-3-yl group, which is substituted in the 1-position by a tert-butyloxycarbonyl or methylsulphonyl group, a piperidin-4-yl group, a piperidin-4-yl group, which is substituted in the 1-position by a methyl, (aminocarbonyl)methyl, (dimethylaminocarbonyl)methyl, (morpholin-4-ylcarbonyl)-methyl, 2-(tert-butyloxycarbonylamino)ethyl, 2-aminoethyl, 2-(acetylamino)ethyl, 2-(methylsulphonylamino)ethyl, cyano, acetyl, methoxyacetyl, (dimethylamino)acetyl, (morpholin-4-yl)acetyl, tetrahydropyran-4-ylcarbonyl, ethylaminocarbonyl, isopropylaminocarbonyl, dimethylaminocarbonyl, diethylaminocarbonyl, pyrrolidin-1-ylcarbonyl, piperidin-1-ylcarbonyl, morpholin-4-ylcarbonyl, 2-methylmorpholin-4-ylcarbonyl, 2,6-di-methylmorpholin-4-ylcarbonyl, homomorpholin-4-ylcarbonyl, 4-methylpiperazin-1-yl-carbonyl, isopropyloxycarbonyl, tert-butyloxycarbonyl, methylsulphonyl, dimethylamino-sulphonyl or morpholin-4-ylsulphonyl group, or a tetrahydrofuran-3-yl, tetrahydropyran-3-yl or tetrahydropyran-4-yl group, $R^d$ is a methoxy, ethyloxy or a 2-(methoxy)ethyloxy group, and X is a nitrogen atom, or a tautomer or salt thereof.

5. A compound in accordance with claim 1, in which $R^a$ is a hydrogen atom, $R^b$ is a 1-phenylethyl group, $R^c$ is a piperidin-4-yl group, a piperidin-4-yl group, which is substituted in the 1-position by a methyl, cyano, acetyl, morpholin-4-ylcarbonyl, tert-butyloxycarbonyl or methylsulphonyl group, $R^d$ is a methoxy group and X is a nitrogen atom, or a tautomer or salt thereof.

6. A physiologically tolerable salt of a compound in accordance with any one of claims 1, 2, 3, 4, or 5.

7. A pharmaceutical composition comprising a compound according to any one of claims 1, 2, 3, 4 or 5 or a physiologically tolerable salt according to claim 6, and a pharmaceutically acceptable carrier or diluent.

8. A method for the treatment of benign or malignant tumours associated with non-small-cell lung cancer and pancreatic cancer which method comprises the administration of a therapeutically effective amount of a compound in accordance with any one of claims 1, 2, 3, 4, 5 or 6.

* * * * *